US007135570B2

(12) United States Patent
McEachern et al.

(10) Patent No.: US 7,135,570 B2
(45) Date of Patent: Nov. 14, 2006

(54) SYNTHESIS OF ENANTIOMERICALLY PURE AMINO-SUBSTITUTED FUSED BICYCLIC RINGS

(75) Inventors: Ernest J. McEachern, White Rock (CA); Gary J. Bridger, Bellingham, WA (US); Krystyna A. Skupinska, New Westminster (CA); Renato T. Skerlj, Vancouver (CA); Wen Yang, Aldergrove (CA)

(73) Assignee: Anormed Inc., Langley (CA)

( * ) Notice: Subject to any disclaimer, the term of this patent is extended or adjusted under 35 U.S.C. 154(b) by 0 days.

(21) Appl. No.: 10/959,823

(22) Filed: Oct. 6, 2004

(65) Prior Publication Data

US 2005/0080267 A1  Apr. 14, 2005

Related U.S. Application Data

(62) Division of application No. 10/243,434, filed on Sep. 12, 2002, now Pat. No. 6,825,351.

(60) Provisional application No. 60/323,201, filed on Sep. 12, 2001.

(51) Int. Cl.
 *C07D 215/00* (2006.01)
(52) U.S. Cl. ............. 546/139; 546/152; 564/305
(58) Field of Classification Search ............. 546/139, 546/152; 564/305
See application file for complete search history.

(56) References Cited

U.S. PATENT DOCUMENTS

| 5,563,151 A | 10/1996 | Bowles |
| 5,583,131 A | 12/1996 | Bridger |
| 5,698,546 A | 12/1997 | Bridger |
| 5,817,807 A | 10/1998 | Bridger |
| 5,932,749 A | 8/1999 | Li |
| 6,365,583 B1 | 4/2002 | MacFarland |

FOREIGN PATENT DOCUMENTS

| WO | WO-99/31264 | 6/1999 |
| WO | WO-99/32100 | 7/1999 |
| WO | WO-00/45814 | 8/2000 |
| WO | WO-00/56729 | 9/2000 |

OTHER PUBLICATIONS

Alreja et al., Heterocycles (1986) 24:1637.
Ami and Horui, Biosci. Biotechnol. Biochem. (1999) 63:2150-2156.
Balkenkohl et al., J. Prakt. Chem. (1997) 339:381-384.
Biard-Piechaczyk et al., Immunology Letters (1999) 701-3.
Blanco et al., The CXCR4 Antagonist AMD3100 Efficiently Inhibits Cell-Surface-Expressed Human Immunodeficiency Virus Type 1 Envelop-Induced Apoptosis American Society for Microbiology, Jan. 2000, pp. 51-56.
Bosch et al., Bioorganic & Medicinal Chemistry Letters (2000) 10:563-566.
Campos et al., Tetrahedron:Asymmetry (2000) 11:2705-2717.
Carrea and Riva, Angew. Chem. Int. Ed. Engl. (1999) 39:2226.
Cliffe et al., Tetrahedron Letters (1991) 32(46):6789-6792.
Crossley et al., journal? 977-982.
De Castro et al., Tetrahedron (2000) 56:1387-1391.
Fedyk et al., Journal of Leukocyic Biology 66:667.
Glase et al., J. Med. Chem. (1995) 38:3132-3137.
Gotor, Biocat. Biotrans. (2000) 18:87.
Greene and Wuts, Protective Groups in Organic Synthesis, 3rd edition, Wiley-Interscience, New York (1999) pp. 552-564.
Gupta et al., J. Biol. Chem. (1998) 7:4282-4287.
Gutman et al., Tetrahedron:Asymmetry (1998) 9:4369.
Hacking et al., Mol. Catalysis B:Enzymatic (2000) 9:201-208.
Herbein et al., Nature (1998) 395:189-193.
Hesselgesser et al., Current Biology, (1997) 7(2):112-121.
Hesselgesser et al. Current Biology (1998) 8(10):595-598.
Honel and Vierhapper, J. Chem. Soc. Perkin. I. (1980) 1933-1939.
Honel and Vierhapper, Monatshefte für Chemie (1984) 115:1219-1228.
Iglesias et al., Tet. Asym. (1997) 8:2675-2677.
International Search Report for PCT/US02/29372, mailed on Aug. 10, 2004, 4 pages.
Kato et al., Enantiomer (2000) 5:521-524.
Kazlauskas and Weissfloch, J. of Molecular Catalysis B:Enzymatic (1997) 3:65-72.
Kitaguchi et al., Am. Chem. Soc. (1989) 111:3094-3095.
Koeller and Wong, Nature (2001) 409:232.
Koltunov and Repinskaya, Russ. J. Org. Chem. (2000) 36:446-447.
Lardenois et al., Synth. Comm. (1996) 26:2305.
Lee et al., Blood (1999) 93(4):1145-1156.
Luna et al. Tet. Asym. (1998) 9:4483-4487.
Maestro et al., Tetrahedron:Assymetry (1997) 8:3153-3159.
Messina et al., J. Org. Chem. (1999) 64:3767-3769.
Morgan et al., J. Org. Chem. (2000) 65:5451-5459.

(Continued)

*Primary Examiner*—Zinna N. Davis
(74) *Attorney, Agent, or Firm*—Morrison & Foerster LLP

(57) ABSTRACT

This invention describes various processes for synthesis and resolution of racemic amino-substituted fused bicyclic ring systems. One process utilizes selective hydrogenation of an amino-substituted fused bicyclic aromatic ring system. An alternative process prepares the racemic amino-substituted fused bicyclic ring system via nitrosation. In addition, the present invention describes the enzymatic resolution of a racemic mixture to produce the (R)— and (S)— forms of amino-substituted fused bicyclic rings as well as a racemization process to recycle the unpreferred enantioner. Further provided by this invention is an asymmetric synthesis of the (R)— or (S)— enantiomer of primary amino-substituted fused bicyclic ring systems.

10 Claims, No Drawings

OTHER PUBLICATIONS

Nikolic et al., Nature (1998) 395:194.
Ohagen et al., Journal of Virology (1999) 73(2):897-906.
Okazaki et al., Bull. Chem. Soc. Jpn. (1990) 63:3167.
Orsat et al., J. Am. Chem. Soc. (1996) 118:712-713.
Ponath, Exp. Opin. Invest. Drugs (1998) 7:1-18.
Pozo and Gotor, Tetrahedron (1993) 49:4321-4326.
Reetz and Dreisbach, Chimia (1994) 48:570.
Rylander, Catalytic Hydrogenation over Platinum Metals, Academic Press, New York (1967) p. 385.
Sanchez et al. Tet. Asym. (1997) 8:37-40.
Schoffers et al., Tetrahedron (1996) 52:3769-3826.
Schramm et al., Journal of Virology (2000) vol. ?:184-192.
Sharma et al., Synthesis (1981) 316-318.
Shiotani et al., Yakugaku Zasshi (1967) 87:547-549.
Smidt et al., Biotechnology Techniques (1996) 10:335-338.
Sucheck et al., Angew. Chem. Int. Ed. (2000) 39(6):1080-1084.
Supplementary European Search Report for EP 02 77 5823, mailed on Dec. 23, 2004, 3 pages.
Tagawa et al., Heterocycles (1989) 29:1741.
Tagawa et al., Heterocycles (1989) 29:1781.
Tagawa et al., Heterocycles (1992) 33:327.
Tagawa et al., Heterocycles (1992) 34:1605.
Takayama et al., Chem. Soc. Chem. Commun. (1999) 2:127-128.
Takayama et al., Tet. Lett. (1996) 37:6287-6290.
Tanida et al., J. of Heterocyclic Chemistry (1986) 23:177-181.
Van Langen et al., Tetrahedron: Asymmetry (2000) 11:4593-4600.
Van Rantwijk et al., Monat. Chem. (2000) 131:549.
Vierhapper and Eliel, J. Am. Chem. Soc. (1974) 96:2256-2257.
Vierhapper and Eliel, J. Org. Chem. (1975) 40:2729-2734.
Vierhapper and Honel, Monat. Chem. (1984) 115:1219-1228.
Wagegg et al., Journal of Biotechnology (1998) 61:75-78.
Wang et al., J. Org. Chem. (1997) 62:3488-3495.

SYNTHESIS OF ENANTIOMERICALLY PURE AMINO-SUBSTITUTED FUSED BICYCLIC RINGS

This application is a divisional application of U.S. Ser. No. 10/243,434 filed Sep. 12, 2002 now U.S. Pat. No. 6,825,351 which claims benefit under 35 U.S.C. § 119(e) of U.S. Ser. No. 60/323,201, filed Sep. 12, 2001. The contents of these applications are incorporated herein by reference.

TECHNICAL FIELD

This invention describes various processes for synthesis and resolution of racemic amino-substituted fused bicyclic ring systems, in particular, amino-substituted tetrahydroquinolines or tetrahydroisoquinolines. One process utilizes selective hydrogenation of an amino-substituted fused bicyclic ring. An alternative process prepares a racemic amino-substituted fused bicyclic ring system via nitrosation. In addition, the present invention describes the enzymatic resolution of a racemic mixture to produce the (R)— and (S)— forms of amino-substituted fused bicyclic ring systems, such as amino-substituted 5,6,7,8-tetrahydroquinoline or 5,6,7,8-tetrahydroisoquinoline. Another aspect of the invention describes a process to racemize the enantiomerically enriched (R)— and (S)— forms of amino-substituted fused bicyclic ring systems. Further provided by this invention is an asymmetric synthesis of an amino-substituted fused bicyclic ring to produce the desired enantiomer.

BACKGROUND OF THE INVENTION

It is desired by those of skill in the art to produce enantiomeric forms of pharmaceutical compounds, since such enantiomers often have increased activity for selected diseases when compared with the racemic form of the same compound. For example, 8-amino-5,6,7,8-tetrahydroquinolines are utilized as intermediates in the preparation of novel heterocyclic compounds that bind to chemokine receptors and demonstrate protective effects against infection of target cells by human immunodeficiency virus (HIV). See WO 00/56729.

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1–18, 1998). These chemotactic cytokines, or chemokines, constitute a family of proteins, approximately 8–10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR".

Chemokines are considered to be principal mediators in the initiation and maintenance of inflammation. More specifically, chemokines have been found to play an important role in the regulation of endothelial cell function, including proliferation, migration and differentiation during angiogenesis and re-endothelialization after injury (Gupta et al., *J. Biolog. Chem.*, 7:4282–4287, 1998). Two specific chemokines have been implicated in the etiology of infection by human immunodeficiency virus (HIV).

For example, U.S. Pat. No. 5,583,131, U.S. Pat. No. 5,698,546 and U.S. Pat. No. 5,817,807 disclose cyclic compounds that are active against HIV-1 and HIV-2. These compounds exhibit anti-HIV activity by binding to the chemokine receptor CXCR4 expressed on the surface of certain cells of the immune system. This competitive binding thereby protects these target cells from infection by HIV which utilizes the CXCR-4 receptor for entry. In addition, these compounds antagonize the binding, signaling and chemotactic effects of the natural CXC-chemokine for CXCR-4, stromal cell-derived factor 1 α (SDF-1).

Additionally cyclic polyamine antiviral agents described in the above-mentioned patents have the effect of enhancing production of white blood cells as well as exhibiting antiviral properties. See U.S. Pat. No. 6,365,583. Thus, these agents are useful for controlling the side-effects of chemotherapy, enhancing the success of bone marrow transplantation, enhancing wound healing and burn treatment, as well as combating bacterial infections in leukemia.

Therefore, a skilled artisan would be interested in more effective and efficient processes for producing racemates and enantiomers of various ring systems. This invention provides such processes.

SUMMARY OF THE INVENTION

The invention provides a process for synthesizing a racemic amino-substituted 5,6,7,8-tetrahydroquinoline or a racemic amino-substituted 5,6,7,8-tetrahydroisoquinoline comprising:

a) reacting an amino-substituted quinoline of the formula I or an amino-substituted isoquinoline of the formula II with an amine-protecting group compound in an organic solvent to produce an amine-protected, substituted quinoline or isoquinoline:

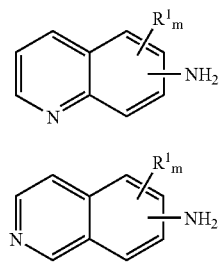

b) hydrogenating the amine-protected, substituted quinoline or isoquinoline in a strongly acidic solvent at an elevated temperature to form the 5,6,7,8-tetrahydroquinoline or 5,6,7,8-tetrahydroisoquinoline; and c) hydrolyzing the amine-protecting group to produce the desired racemic amino-substituted 5,6,7,8-tetrahydroquinoline or racemic amino-substituted 5,6,7,8-tetrahydroisoquinoline;

wherein $NH_2$ is located at any position on the benzene portion of the quinoline or isoquinoline, $R^1$ is located at any other hydrogen position on the quinoline or isoquinoline ring; m is 0–4; and wherein $R^1$ is selected from the group consisting of nitro, cyano, carboxylic acid, alkyl, alkoxy, cycloalkyl, a protected hydroxyl, a protected thiol, a protected amino, acyl, carboxylate, carboxamide, sulfonamide, an aromatic group and a heterocyclic group.

The invention also provides a process for synthesizing a racemic amino-substituted 5,6,7,8-tetrahydroquinoline or a racemic amino-substituted 5,6,7,8-tetrahydroisoquinoline comprising:

a) reacting either a substituted 5,6,7,8-tetrahydroquinoline of the formula III or a substituted 5,6,7,8-tetrahydroisoquinoline of the formula IV

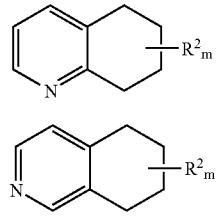

with at least 2 equivalents of an alkyllithium base, or a lithium, sodium, or potassium amide base, and then with a nitrosating agent to form an oxime; and b) reducing the oxime to produce the racemic amino-substituted 5,6,7,8-tetrahydroquinoline or the racemic amino-substituted 5,6,7,8-tetrahydroisoquinoline;

wherein the amino is located at the 8-position on the quinoline or the 5-position on the isoquinoline; $R^2$ is located at any other hydrogen position on the quinoline or isoquinoline ring; m is 0–4; and wherein $R^2$ is selected from the group consisting of halo, nitro, cyano, a protected carboxylic acid, alkyl, alkenyl, cycloalkyl, a protected hydroxyl, a protected thiol, a protected amino, acyl, carboxylate, carboxamide, sulfonamide, an aromatic group and a heterocyclic group.

Further provided is a process for synthesizing a keto-substituted 5,6,7,8-tetrahydroquinoline or a keto-substituted 5,6,7,8-tetrahydroisoquinoline comprising:

a) reacting either a substituted 5,6,7,8 tetrahydroquinoline of the formula III or a substituted 5,6,7,8-tetrahydroisoquinoline of the formula IV

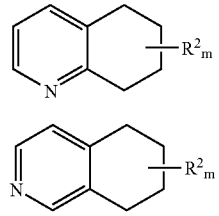

with at least 2 equivalents of an alkyllithium base, or a lithium, sodium, or potassium amide base; and then with a nitrosating agent to form an oxime; and b) hydrolyzing the oxime to produce the corresponding ketone;

wherein the keto is located at the 8-position on the quinoline or the 5-position on the isoquinoline; $R^2$ is located at any other hydrogen position on the quinoline or isoquinoline; m is 0–4; and $R^2$ is selected from the group consisting of halo, nitro, cyano, a protected carboxylic acid, alkyl, alkenyl, cycloalkyl, a protected hydroxyl, a protected thiol, a protected amino, acyl, carboxylate, carboxamide, sulfonamide, an aromatic group, and a heterocyclic group.

Also, this invention provides a process for resolving racemic amino-substituted 5,6,7,8-tetrahydroquinoline of the formula V or racemic amino-substituted 5,6,7,8-tetrahydroisoquinoline of the formula VI to produce the two enantiomers,

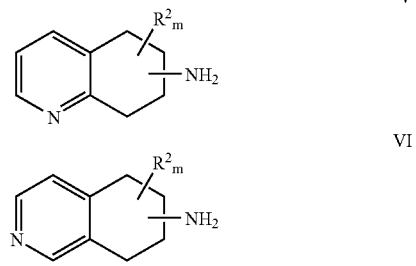

comprising:

a) enantioselectively acylating or carbamoylating the racemic amino-substituted 5,6,7,8-tetrahydroquinoline or the racemic amino-substituted 5,6,7,8-tetrahydroisoquinoline using an enantioselective enzyme as a catalyst; and b) separating the unreacted amino-substituted 5,6,7,8-tetrahydroquinoline or 5,6,7,8-tetrahydroisoquinoline as the first enantiomer, from the enantiomeric amide-or carbamate-substituted 5,6,7,8-tetrahydroquinoline or 5,6,7,8-tetrahydroisoquinoline; and c) cleaving the amide or carbamate group to isolate the second enantiomer of the amino-substituted 5,6,7,8-tetrahydroquinoline or 5,6,7,8-tetrahydroisoquinoline;

wherein $NH_2$ is located at any position on the saturated portion of the quinoline or isoquinoline; $R^2$ is located at any other hydrogen position on the quinoline or isoquinoline ring; m is 0–4; and $R^2$ is selected from the group consisting of halo, nitro, cyano, carboxylic acid, alkyl, alkenyl, cycloalkyl, hydroxyl, thio, a protected amino, acyl, carboxylate, carboxamide, sulfonamide, an aromatic group and a heterocyclic group.

Another process is provided for resolving racemic amino-substituted 5,6,7,8-tetrahydroquinoline of the formula V or amino-substituted 5,6,7,8-tetrahydroisoquinoline of the formula VI to produce one of the enantiomers,

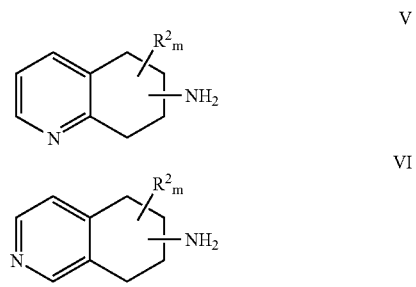

comprising:

a) enantioselectively acylating or carbamoylating the racemic amino-substituted 5,6,7,8-tetrahydroquinoline or the racemic amino-substituted 5,6,7,8-tetrahydroisoquinoline using an enantioselective enzyme as a catalyst to produce a mixture of the corresponding unreacted amine in the first enantiomeric form and the reacted amide or carbamate in the second enantiomeric form; and b) isolating the first enantiomer of the amino-substituted 5,6,7,8-tetrahydroquinoline or 5,6,7,8-tetrahydroisoquinoline;

wherein NH$_2$ is located at any position on the saturated portion of the quinoline or isoquinoline; R$^2$ is located at any other hydrogen position on the quinoline or isoquinoline ring; m is 0–4; and R$^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group.

A process is provided for resolving racemic amino-substituted 5,6,7,8-tetrahydroquinoline or racemic amino-substituted 5,6,7,8-tetrahydroisoquinoline to produce the two enantiomers, comprising:

a) reacting racemic amide- or carbamate-substituted 5,6,7,8-tetrahydroquinoline of the formula VII or racemic amide- or carbamate-substituted 5,6,7,8-tetrahydroisoquinoline of the formula VIII

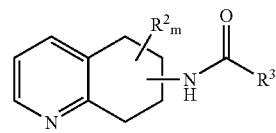

VII

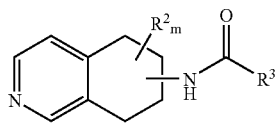

VIII with water, an alcohol, or a primary or secondary amine using an enantioselective enzyme as a catalyst to produce a mixture of the corresponding amine in the first enantiomeric form, and the unreacted amide or carbamate in the second enantiomeric form;

b) separating the first enantiomer of the amino-substituted 5,6,7,8-tetrahydroquinoline or amino-substituted 5,6,7,8-tetrahydroisoquinoline, from the unreacted amide or carbamate; and c) cleaving the amide or carbamate group to produce the second enantiomer of the amino-substituted 5,6,7,8-tetrahydroquinoline or amino-substituted 5,6,7,8-isoquinoline;

wherein the amide or carbamate group is located at any position on the saturated portion of the quinoline or isoquinoline; R$^2$ is located at any other hydrogen position on the quinoline or isoquinoline ring; m is 0–4; R$^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and R$^3$ is an optionally substituted carbon atom or an optionally substituted oxygen atom.

Additionally, this invention provides a process for resolving racemic amino-substituted 5,6,7,8-tetrahydroquinoline or racemic amino-substituted 5,6,7,8-tetrahydroisoquinoline to produce one of the enantiomers, comprising:

a) reacting racemic amide-or carbamate-substituted 5,6,7,8-tetrahydroquinoline of the formula VII or racemic amide-or carbamate-substituted 5,6,7,8-tetrahydroisoquinoline of the formula VIII

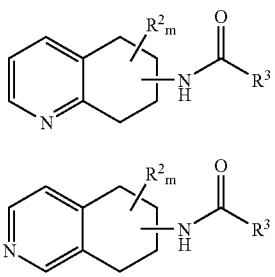

VII

VIII with water, an alcohol, or a primary or secondary amine using an enantioselective enzyme as a catalyst to produce a mixture of the corresponding amine in the first enantiomeric form, and the unreacted amide or carbamate in the second enantiomeric form; and b) isolating the first enantiomer of the amino-substituted 5,6,7,8-tetrahydroquinoline or 5,6,7,8-tetrahydroisoquinoline;

wherein the amide or carbamate is located at any position on the saturated portion of the quinoline or isoquinoline; R$^2$ is located at any other hydrogen position on the quinoline or isoquinoline ring; m is 0–4; R$^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and R$^3$ is an optionally substituted carbon atom or an optionally substituted oxygen atom.

A process is provided for racemizing an enantiomerically enriched amino-substituted 5,6,7,8-tetrahydroquinoline of the formula XIII or amino-substituted 5,6,7,8-tetrahydroisoquinoline of the formula XIV to produce the corresponding racemic mixture:

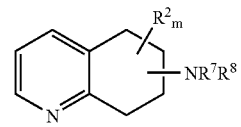

XIII

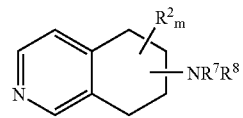

XIV comprising:

a) heating the enantiomerically enriched amino-substituted 5,6,7,8-tetrahydroquinoline or amino-substituted 5,6,7,8-tetrahydroisoquinoline neat or in an organic solvent in the presence or absence of an additive; and b) when either R$^7$ or R$^8$ is not hydrogen, cleaving the R$^7$ or R$^8$ group under conditions to form the corresponding amino;

wherein NR$^7$R$^8$ is located at any position on the saturated portion of the quinoline or isoquinoline; R$^2$ is located at any other hydrogen position on the quinoline or isoquinoline ring; m is 0–4;

R$^2$ is selected from the group consisting of halo, nitro, cyano, carboxylic acid, alkyl, alkenyl, cycloalkyl, hydroxyl, thio, a protected amino, acyl, carboxylate, carboxamide, sulfonamide, an aromatic group, and a heterocyclic group; and $R^7$ and $R^8$ are each selected from the group consisting of hydrogen, alkyl, aryl, heteroalkyl, heteroaryl, aralkyl, alkanoyl, alkylsulfonyl, a carbonyl- or sulfonyl-group substituted by an aromatic or heterocyclic ring, aryloxycarbonyl, alkoxycarbonyl, arylcarbamoyl, alkylcarbamoyl, arylthiocarbonyl, alkylthiocarbonyl, and carbamoyl.

A process is provided for synthesizing an enantiomer of a primary amino-substituted fused bicyclic ring of formula IX comprising:

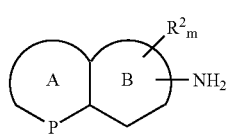

IX a) forming the Schiff base of a keto group located on ring B of the fused bicyclic ring by reacting it with an enantiomerically-pure primary amine chiral auxiliary R*NH$_2$ of the formula X

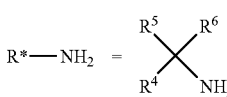

X to produce the corresponding enantiomerically-pure imine of the fused bicyclic ring;

b) diastereoselectively reducing the imine to produce the corresponding enantiomerically-pure secondary amine on the fused bicyclic ring; and c) removing the chiral auxiliary R* to form the enantiomer of the primary amino-substituted fused bicyclic ring;

wherein ring A is a heteroaromatic 5- or 6-membered ring, P is a nitrogen atom, sulfur atom or oxygen atom; ring B is a 5- or 6-membered cycloalkyl or heterocycloalkyl;

wherein NH$_2$ is located at a position on ring B; and $R^2$ is located at any other hydrogen position on the fused bicyclic ring;

wherein m is 0–4; $R^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and $R^4$, $R^5$, and $R^6$ are each different and selected from the group consisting of hydrogen, alkyl, alkenyl, cycloalkyl, cycloalkenyl, and a 5- or 6-membered aromatic ring; and at least one of $R^4$, $R^5$, or $R^6$ is a 5- or 6-membered aromatic ring.

DETAILED DESCRIPTION OF THE INVENTION

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or "l" meaning that the compound is "levorotatory" and with (+) or "d" meaning that the compound is "dextrorotatory". There is no correlation between the nomenclature for the absolute stereochemistry and for the rotation of an enantiomer. For a given chemical structure, these compounds, called "stereoisomers", are identical except that they are mirror images of one another. A specific stereoisomer can be referred to as an "enantiomer" and a mixture of such isomers is often called an "enantiomeric" or "racemic" mixture. See e.g., Streitwiesser, A. & Heathcock, C. H., INTRODUCTION TO ORGANIC CHEMISTRY, 2nd Edition, Chapter 7 (MacMillan Publishing Co., USA, 1981). In the present application, the designation (R,S) represents the racemic mixture of the R— and S— enantiomers and the individual enantiomers also can be designated as, for example, (8R)— and/or (8S)— amino-5,6,7,8-tetrahydroquinoline.

"Enantiomerically pure" or "enantiomerically enriched" or "optically pure" or "substantially optically pure" or "enantiopure" as used herein means that the enantiomer or isomer is substantially free of the alternative enantiomer or isomer, wherein the composition is at least 90% by weight of the desired isomer and 10% by weight or less of the alternate isomer. In a more preferred embodiment, the terms mean that the composition is at least 99% by weight of the desired isomer and 1% by weight or less of the alternative isomer or enantiomer. These percentages are based upon the total amount of compound in the composition.

The term "enantiomeric excess" or "ee" is related to the term "optical purity" in that both are measures of the same phenomenon. The value of ee will be a number from 0 to 100, 0 being racemic and 100 being pure, single enantiomer. A compound that is referred to as 98% optically pure can be described as 98% ee. See, e.g., March J., ADVANCED ORGANIC CHEMISTRY: REACTIONS, MECHANISMS AND STRUCTURES, 3rd Edition, Chapter 4 (John Wiley & Sons, USA, 1985). The percent optical purity for a given sample is defined as:

$$\text{Percent optical purity} = \frac{[\alpha]\,obs \times 100}{[\alpha]\text{max}}$$

Where [α] obs is the observed angle of rotation of plan-polarized light and [α] max is the maximum rotation possible (i.e., the rotation that would be observed for an enantiomerically pure sample). Assuming that there is a linear relationship between [α] and concentration, then the optical purity is equal to the percent excess of one enantiomer over the other:

$$\text{optical purity} = \text{enantiomeric excess } (ee)$$
$$= \frac{[R]-[S]}{[R]+[S]} \times 100 = \%R - \%S.$$

The substituent groups defined below can be optionally substituted; therefore, for example, when the term "alkyl" is utilized, it also encompasses substituted alkyls.

General structures are defined as follows: wherein, ring A or ring C is an optionally substituted heteroaromatic 5- or 6-membered ring, and P is an optionally substituted carbon atom, an optionally substituted nitrogen atom, sulfur or oxygen atom. Ring B or ring D is an optionally substituted saturated or partially saturated carbon 5- to 6-membered cycloalkyl or heterocycloalkyl.

Examples of the optionally substituted 5- or 6-membered ring A or ring C are pyridine, pyrimidine, pyrazine, pyridazine, triazine, imidazole, pyrazole, triazole, oxazole, thiazole. Six-membered rings are preferred for ring A or ring C, particularly pyridine.

Examples of the optionally substituted ring B or ring D are cyclohexane, piperidine, piperazine, hexahydropyridazine, tetrahydrofuran, tetrahydrothiophene, tetrahydropyran, and tetrahydrothiapyran, with the preferred combination of rings A and B, or C and D, being 5,6,7,8-tetrahydroquinoline and 5,6,7,8-tetrahydroisoquinoline.

In the above examples, the "optional substituents" in Rings A, B, C, and D may be nitro, cyano, carboxylic acid, an optionally substituted alkyl or cycloalkyl groups, an optionally substituted hydroxyl group, an optionally substituted thiol group, an optionally substituted amino or acyl group, an optionally substituted carboxylate, carboxamide or sulfonamide group, an optionally substituted aromatic or heterocyclic group.

Examples of the optionally substituted alkyl include $C_{1-12}$ alkyl, including methyl, ethyl, propyl etc. and examples of the optionally substituted cycloalkyl groups include $C_{3-10}$ cycloalkyl such as cyclopropyl, cyclobutyl, cyclopentyl, cyclohexyl, cycloheptyl, etc. In these cases, $C_{1-6}$ alkyl and cycloalkyl are preferred. The optional substituent may also be an optionally substituted aralkyl (e.g. phenyl $C_{1-4}$ alkyl) or heteroalkyl for example, phenylmethyl (benzyl), phenethyl, pyridinylmethyl, pyridinylethyl etc. The heterocyclic group may be a 5- or 6-membered ring containing 1–4 heteroatoms.

Examples of the optionally substituted hydroxyl and thiol groups include an optionally substituted alkyl (e.g. $C_{1-10}$ alkyl) such as methyl, ethyl, propyl, isopropyl, butyl, isobutyl, sec-butyl, tert-butyl, pentyl etc., preferably ($C_{1-6}$) alkyl; an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted aralkyl (e.g. phenyl-$C_{1-4}$ alkyl, e.g. benzyl, phenethyl, etc.). Where there are two adjacent hydroxyl or thiol substituents, the heteroatoms may be connected via an alkyl group such as $O(CH_2)_nO$ and $S(CH_2)_nS$ (where n=1–5). Examples include methylenedioxy, ethylenedioxy etc. Oxides of thio-ether groups such as sulfoxides and sulfones are also encompassed.

Further examples of the optionally substituted hydroxyl group include an optionally substituted $C_{2-4}$ alkanoyl (e.g. acetyl, propionyl, butyryl, isobutyryl, etc.), $C_{1-4}$ alkylsulfonyl (e.g. methanesulfonyl, ethanesulfonyl, etc.) and an optionally substituted aromatic and heterocyclic carbonyl group including benzoyl, pyridinecarbonyl etc.

The substituents on the optionally substituted amino group may bind to each other to form a cyclic amino group (e.g. 5- to 6-membered cyclic amino, etc. such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.) the number of preferred substituents are 1 to 3.

The amino group may also be substituted once or twice (to form a secondary or tertiary amine) with a group such as an optionally substituted alkyl group including $C_{1-10}$ alkyl (e.g. methyl, ethyl propyl etc.) or an optionally substituted cycloalkyl group such as cyclopropyl, cyclobutyl, cyclopentyl, cyclohexyl, cycloheptyl, etc. In these cases, $C_{1-6}$ alkyl and cycloalkyl are preferred. The amine group may also be optionally substituted with an aromatic or heterocyclic group, aralkyl (e.g. phenyl $C_{1-4}$ alkyl) or heteroalkyl for example, phenyl, pyridine, phenylmethyl (benzyl), phenethyl, pyridinylmethyl, pyridinylethyl etc. The heterocyclic group may be a 5- or 6-membered ring containing 1–4 heteroatoms. The optional substituents of the "optionally substituted amino groups" are the same as defined above for the "optionally substituted cyclic amino group."

The amino group may be substituted with an optionally substituted $C_{2-4}$ alkanoyl e.g. acetyl, propionyl, butyryl, isobutyryl etc., or a $C_{1-4}$ alkylsulfonyl (e.g. methanesulfonyl, ethanesulfonyl, etc.) or a carbonyl or sulfonyl substituted aromatic or heterocyclic ring, e.g. benzenesulfonyl, benzoyl, pyridinesulfonyl, pyridinecarbonyl etc. The heterocycles are as defined above. The optional substituents on the amine substituents described above are the same as defined above for the "optionally substituted cyclic amino group."

Examples of the optionally substituted acyl group as the substituents on the rings A, B, C, and D include a carbonyl group or a sulfonyl group binding to hydrogen; an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted 5- to 6-membered monocyclic aromatic group (e.g. phenyl, pyridyl, etc.).

Examples of the optionally substituted carboxylate group (ester groups) include an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.); an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted aryl (e.g. phenyl, naphthyl, etc.) and $C_{1-4}$ aryl for example, benzyl, phenethyl etc. Groups such as methoxymethyl, methoxyethyl etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups as substituents for Rings A, B, C, and D are phenyl, naphthyl, or a 5- or 6-membered heterocyclic ring containing 1–4 heteroatoms. The optional substituents are essentially identical to those listed above for Rings A, B, C, and D.

In the above examples the number of substituents on Rings A, B, C, and D may be 1–4, preferably 1–2. The substituents on the optionally substituted groups are the same as the optionally substituted groups described above. Preferred substituents are halogen (fluorine, chlorine etc.), nitro, cyano, hydroxy group, thiol group, amino group, carboxyl group, carboxylate group, sulfonate group, sulfonamide group, carboxamide group, an optionally halogenated $C_{1-4}$ alkoxy (e.g. trifluoromethoxy, etc.), $C_{2-4}$ alkanoyl (e.g. acetyl, propionyl, etc.) or aroyl, a $C_{1-4}$ alkylsulfonyl (e.g. methanesulfonyl, ethanesulfonyl, etc.), an optionally substituted aryl or heterocyclic group. The number of substituents on the said groups are preferably 1 to 3.

The preferred substituent for rings A, B, C, and D is an amino group substituted with an optionally substituted $C_{2-4}$ alkanoyl e.g. acetyl, propionyl, butyryl, isobutyryl etc., or a $C_{1-4}$ alkylsulfonyl (e.g. methanesulfonyl, ethanesulfonyl, etc.) or a carbonyl or sulfonyl substituted aromatic or heterocyclic ring; most preferable is an acetyl-substituted amino group.

For the amide substituent, examples include an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted 5- to 6-membered monocyclic aromatic group (e.g. phenyl, pyridyl, etc.). The optional substituents may also be an optionally substituted aralkyl (e.g. phenyl $C_{1-4}$ alkyl) or heteroalkyl for example, phenylmethyl (benzyl), phenethyl, pyridinylmethyl, pyridinylethyl etc. The heterocyclic group may be a 5- or 6-membered ring containing 1–4 heteroatoms. Optional substituents also include halogens (fluorine, chlorine, bromine, etc.) and optionally substituted heteroatoms such as oxygen, sulfur, nitrogen, etc.

Amine groups can be protected from reactivity during a particular part of a process by groups such as acyls, carbamates, enamines, or sulfonamides, and the like. Hydroxyls can be protected via ketones, esters or ethers; carboxylic acids and thiols can be protected by esters or ethers.

The present invention describes various methods for synthesizing and resolving the enantiomeric forms of amino-substituted bicyclic fused ring systems as described below.

Selective Hydrogenation Process

This invention provides for the selective hydrogenation of a fused bicyclic ring system. The system comprises an optionally-substituted 5- or 6-membered heteroaromatic ring fused to an optionally-substituted 5- or 6-membered heteroaromatic or aromatic ring, wherein the fused bicyclic ring system also comprises an amino group at any position, except at the location of a heteroatom or at the location of a ring fusion. The heteroaromatic ring includes: pyridine, pyrimidine, pyrazine, pyridazine, triazine, imidazole, pyrazole, triazole, oxazole, and thiazole. Six-membered rings are preferred for both rings, and quinolines and isoquinolines are most preferred for the fused bicyclic ring system.

A process is provided for synthesizing a racemic amino-substituted 5,6,7,8-tetrahydroquinoline or a racemic amino-substituted 5,6,7,8-tetrahydroisoquinoline comprising:

a) reacting an amino-substituted quinoline of the formula I or an amino-substituted isoquinoline of the formula II with an amine-protecting group compound in an organic solvent to produce an amine-protected, substituted quinoline or isoquinoline:

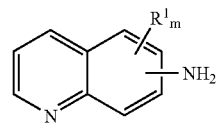

I

-continued

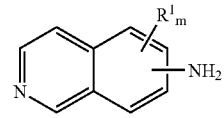

II b) hydrogenating the amine-protected, substituted quinoline or isoquinoline in a strongly acidic solvent at an elevated temperature to form the 5,6,7,8-tetrahydroquinoline or 5,6,7,8-tetrahydroisoquinoline; and c) hydrolyzing the amine-protecting group to produce the desired racemic amino-substituted 5,6,7,8-tetrahydroquinoline or racemic amino-substituted 5,6,7,8-tetrahydroisoquinoline;

wherein $NH_2$ is located at any position on the benzene portion of the quinoline or isoquinoline, $R^1$ is located at any other hydrogen position on the quinoline or isoquinoline ring; m is 0–4; and wherein $R^1$ is selected from the group consisting of nitro, cyano, carboxylic acid, alkyl, alkoxy, cycloalkyl, a protected hydroxyl, a protected thiol, a protected amino, acyl, carboxylate, carboxamide, sulfonamide, an aromatic group and a heterocyclic group.

For example, a preferred process for the synthesis of racemic 8-amino-5,6,7,8-tetrahydroquinoline using selective hydrogenation is described. (Scheme 1). The protocol involves starting with 8-aminoquinoline 1, which is commercially available, and acetylating it to form the corresponding acetamide derivative 2: N-(quinoline-8-yl)-acetamide, using acetic anhydride in an organic solvent. Subsequent hydrogenation of the acetamide in a strongly acidic solvent at an elevated temperature forms the 5,6,7,8-tetrahydroquinoline 3, and then the acetamide is cleaved via acid hydrolysis to produce the desired racemic mixture or (R,S)-8-amino-5,6,7,8-tetrahydroquinolines 4.

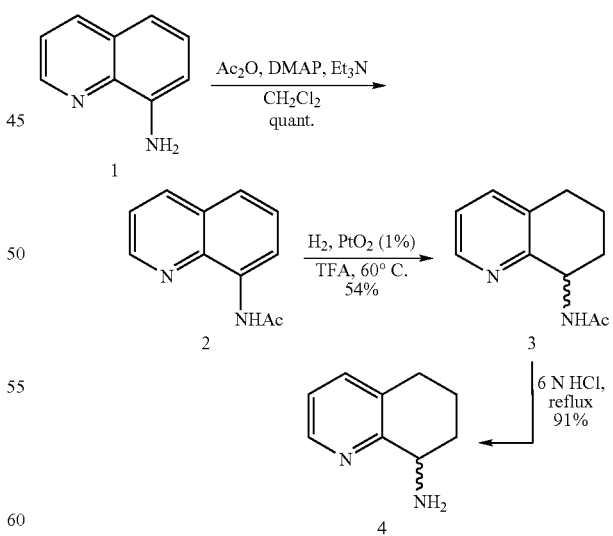

An amino-substituted quinoline or isoquinoline is reacted with an amine protecting group in an organic solvent to produce an amine-protected quinoline or isoquinoline. The protecting group is utilized to prevent hydrogenolysis of the desired amine during the hydrogenation. Therefore, any amine protecting group can be used, such as, an acyl, carbamate, or sulfonamide, and the like. The preferred amine protecting group is an acetyl. The amino substituted compound is reacted with acetic anhydride to form the acetamide wherein the organic solvent is triethylamine ($Et_3N$) in dichloromethane with 4-dimethylaminopyridine (DMAP) as a catalyst.

The hydrogenation is carried out in a strongly acidic solvent, such as trifluoroacetic acid, hydrofluoric acid, hydrochloric acid, hydrobromic acid, sulfuric acid, phosphoric acid, trichloroacetic acid, acetic acid, or any combination thereof. The preferred solvent is trifluoroacetic acid.

Catalysts for the hydrogenation can include: platinum black, platinum on carbon (0.5–20%), platinum on alumina (0.5–20%), platinum (IV) oxide, platinum (IV) oxide hydrate (Adam's catalyst), any other salts or covalent compounds or coordination complexes of platinum that lead to the generation of an active platinum (0) catalyst under the reaction conditions. The preferred catalysts include platinum (IV) oxide and Adam's catalyst. Catalyst loading is typically from 0.1% to 50% by weight, with the most preferred catalyst loading being 1 to 3% by weight.

The reaction temperatures for the hydrogenation reaction are typically elevated, with the temperature range from about 50 to about 150° C. with the preferred temperature being from about 50 to about 70° C. and about 60° C. being the most preferred. However, the hydrogenation reaction can be conducted from about 20 to 50° C. if desired.

The reaction concentration is from about 0.01M to about 5M with the preferred concentration from about 0.2M to about 0.5M; whereas, the hydrogen pressure is from about 0.1 to about 100 atmospheres, with the preferred pressure at about 1 atmosphere. Reaction times are from about 30 minutes to about 2 days and the preferred reaction time is from about 2 to about 18 hours.

Preferably, the hydrogenation is performed with 0.3M of substrate in TFA using 5 mol % of $PtO_2$ at 60° C. under 1 atmosphere of hydrogen. Also preferred is when the amino group is located at the 8-position of the quinoline, m is 0 or 1, and $R^1$ is methyl or methoxy.

Hydrolysis of the amide group to provide the corresponding amine is accomplished by standard methods, including, but not limited to, heating with aqueous acid (for example, refluxing in 6N aqueous hydrochloric acid), heating with aqueous base (for example, refluxing in 6N aqueous sodium hydroxide), and heating in an appropriate solvent in the presence of hydrazine.

Nitrosation Process

This invention also provides for the regioselective nitrosation of fused bicyclic ring systems wherein the process involves the metallation of the saturated portion of the bicyclic ring with a strong base, followed by trapping the resultant anion with an appropriate nitrosating agent to give the corresponding nitrosyl compound. Spontaneous intramolecular rearrangement of this intermediate provides the oxime derivative. The oxime may be reduced to form the corresponding amine derivative or may be hydrolyzed to provide the corresponding ketone. The fused bicyclic ring system comprises an optionally-substituted 5- or 6-membered heteroaromatic ring fused to an optionally-substituted 5- or 6-membered partially or fully saturated cycloalkyl or heterocycloalkyl, such as, for example, a 5,6,7,8-tetrahydroquinoline or 5,6,7,8-tetrahydroisoquinoline. The heteroaromatic ring includes: pyridine, pyrimidine, pyrazine, pyridazine, triazine, imidazole, pyrazole, triazole, oxazole and thiazole. The saturated ring includes cyclohexane, piperidine, piperazine, hexahydropyridazine, tetrahydrofuran, tetrahydrothiophene, tetrahydropyran and tetrahydrothiapyran.

A process is described for synthesizing a racemic amino-substituted 5,6,7,8-tetrahydroquinoline or a racemic amino-substituted 5,6,7,8-tetrahydroisoquinoline comprising:

a) reacting either a substituted 5,6,7,8-tetrahydroquinoline of the formula III or a substituted 5,6,7,8-tetrahydroisoquinoline of the formula IV

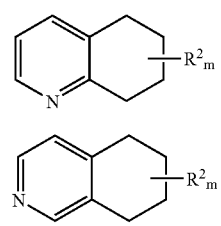

III

IV with at least 2 equivalents of an alkyllithium base, or a lithium, sodium, or potassium amide base, and then with a nitrosating agent to form an oxime; and b) reducing the oxime to produce the racemic amino-substituted 5,6,7,8-tetrahydroquinoline or the racemic amino-substituted 5,6,7,8-tetrahydroisoquinoline;

wherein the amino is located at the 8-position on the quinoline or the 5-position on the isoquinoline; $R^2$ is located at any other hydrogen position on the quinoline or isoquinoline ring; m is 0–4; and wherein $R^2$ is selected from the group consisting of halo, nitro, cyano, a protected carboxylic acid, alkyl, alkenyl, cycloalkyl, a protected hydroxyl, a protected thiol, a protected amino, acyl, carboxylate, carboxamide, sulfonamide, an aromatic group and a heterocyclic group.

Further provided is a process for synthesizing a keto-substituted 5,6,7,8-tetrahydroquinoline or a keto-substituted 5,6,7,8-tetrahydroisoquinoline comprising:

a) reacting either a substituted 5,6,7,8 tetrahydroquinoline of the formula III or a substituted 5,6,7,8-tetrahydroisoquinoline of the formula IV

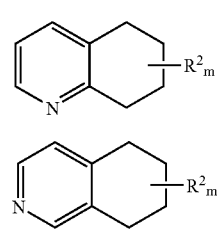

III

IV with at least 2 equivalents of an alkyllithium base, or a lithium, sodium, or potassium amide base; and then with a nitrosating agent to form an oxime; and b) hydrolyzing the oxime to produce the corresponding ketone;

wherein the keto is located at the 8-position on the quinoline or the 5-position on the isoquinoline; $R^2$ is located at any other hydrogen position on the quinoline or isoquinoline; m is 0–4; and $R^2$ is selected from the group consisting of halo, nitro, cyano, a protected carboxylic acid, alkyl, alkenyl, cycloalkyl, a protected hydroxyl, a protected thiol, a protected amino, acyl, carboxylate, carboxamide, sulfonamide, an aromatic group, and a heterocyclic group.

This invention further provides a preferred alternative synthetic route for (R,S)-8-amino-5,6,7,8-tetrahydroquinoline using nitrosation. (Scheme 2). 5,6,7,8-Tetrahydroquinoline 5, which is commercially available, is utilized as the starting material and is reacted with a strong base in an organic ether to deprotonate the tetrahydroquinoline and then the tetrahydroquinoline is reacted with an alkyl nitrite to produce the oxime derivative 6: 6,7-dihydro-5H-quinolin-8-one oxime. Subsequent reduction of the oxime to the amine results in the racemic product 4: (R,S)-8-amino-5,6,7,8-tetrahydroquinoline. Alternatively, the oxime can be hydrolyzed to produce 6,7-dihydro-5H-quinoline-8-one 7.

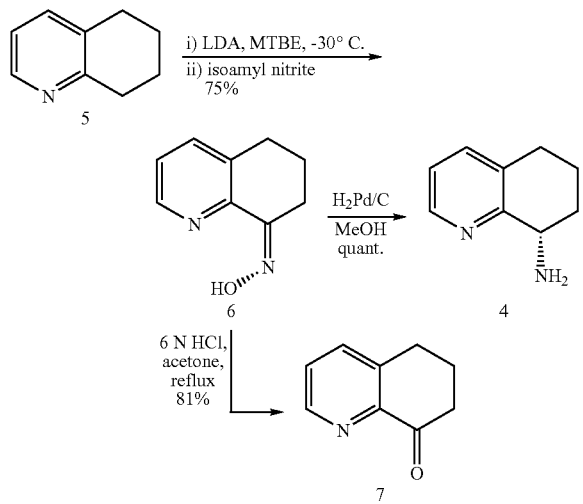

Scheme 2

The nitrosation reaction is carried out in a solvent or combination of solvents, such as ethereal solvents (diethyl ether, diisopropyl ether, dibutyl ether, methyl tert-butyl ether, dipentyl ether, tert-amyl methyl ether, dimethoxy ether, 2-methoxyethyl ether, diethylene glycol dimethyl ether, diphenyl ether, dibenzyl ether, tetrahydrofuran, 1,4-dioxane, or morpholine), aromatic solvents (benzene, toluene, ethylbenzene, o-xylene, m-xylene, p-xylene, mesitylene, chlorobenzene, o-dichlorobenzene, p-dichlorobenzene, 1,2,4-trichlorobenzene, naphthalene, pyridine, furan, or thiophene), dipolar aprotic solvents (carbon disulfide, dimethylformamide, dimethyl sulfoxide, or 1-methyl-2-pyrrolidinone), alkane solvents (petroleum ether, mineral spirits, pentane, hexane, heptane, octane, isooctane, nonane, decane, hexadecane, 2-methylbutane, cyclopentane, or cyclohexane), and alkene solvents (1-pentene, 1-hexene, cyclopentene, or cyclohexene). The most preferred solvents are the ethereal solvents, in particular, diethyl ether, methyl tert-butyl ether, tetrahydrofuran (THF), dimethoxyethane, 2-methoxyethyl ether, and 1,4-dioxane. Preferred additives (activating cosolvents) include tetramethylethylenediamine, pentamethyldiethylenetriamine, dimethylpropyleneurea, or hexamethyl phosphoric triamide, or any combination thereof.

Reaction times for the metallation are from about 5 minutes to about 4 hours, preferably from about 15 minutes to about 1 hour; whereas the reaction time for the nitrosation is from about 5 minutes to about 4 hours, preferably from about 15 minutes to about 2 hours.

For the nitrosation, at least 2 equivalents of base are required, preferably from 2 to 3 equivalents, but less than 10 equivalents. In addition, the base must be sufficiently non-nucleophilic so as not to react with the selected nitrosating agent. Therefore, bases utilized are alkyllithium bases (methyllithium, n-butyllithium, s-butyllithium, tert-butyllithium, isobutyllithium, phenyllithium, ethyllithium, n-hexyllithium, or isopropyllithium), lithium, sodium, or potassium alkoxide bases (sodium methoxide, sodium ethoxide, or sodium ert-butoxide), or lithium, sodium, or potassium amide bases (lithium amide, sodium amide, potassium amide, lithium hexamethyldisilazide, sodium hexamethyldisilazide, potassium hexamethyldisilazide, lithium diisopropylamide, lithium diethylamide, lithium dicyclohexylamide, or lithium 2,2,6,6-tetramethylpiperidide) or any appropriate combination thereof. Preferred bases are n-butyllithium, tert-butyllithium, lithium diisopropylamide, lithium dicyclohexylamide, lithium 2,2,6,6-tetramethylpiperidide (LTMP), and potassium hexamethyldisilazide, with LTMP as more preferred.

The temperature for the nitrosation reaction is from about −100° C. to about 60° C., preferably between about −30° C. and about 0° C.

The concentration for the nitrosation reaction is from about 0.01M to about 10M, preferably from about 0.2 to about 0.5M. Nitrosating agents include: alkyl nitrites (n-butyl nitrite, s-butyl nitrite, tert-butyl nitrite, isobutyl nitrite, isoamyl nitrite, n-amyl nitrite, ethyl nitrite, isopropyl nitrite, or n-propyl nitrite) and alkyl dinitrites (1.3-propane dinitrite, 1,4-butane dinitrite, or 1,5-pentane dinitrite). Preferably the nitrosating agents are tert-butyl nitrite and isoamyl nitrite. The equivalents of nitrosating agent utilized are from about 0.5 to about 10 equivalents with about 2 to about 3 equivalents preferred.

Preferably, nitrosation of 5,6,7,8-tetrahydroquinoline is carried out in THF, at a temperature from about −40° C. to about −78° C., with a concentration of about 0.2M and about 2.5 equivalents of LTMP. Also preferred are wherein the amino group is located at the 8-position of the 5,6,7,8-tetrahydroquinoline or at the 5 position of the 5,6,7,8-tetrahydroisoquinoline; m is 0 or 1; and $R^2$ is methyl.

Reduction of the oxime is accomplished by standard methods, for example, hydrogen, methanol, and 10% palladium on carbon; hydrogen, methanol and Raney nickel; zinc metal in hydrochloric acid; or zinc metal in trifluoroacetic acid. In certain instances, it would be preferable to utilize a chiral hydrogenation catalyst or a chirally-modified reducing agent to enrich the production of the desired enantiomer.

Alternatively, the oxime can be hydrolyzed to provide the ketone via standard methods, such as the use of aqueous 6N hydrochloric acid in acetone under reflux conditions or in aqueous 6N hydrochloric acid under reflux conditions.

Enzymatic Resolution Process

This invention provides for the use of enzymatic methods to resolve racemic mixtures of amino-substituted fused bicyclic ring systems, wherein the enzyme either selectively acylates or carbamoylates the racemic amine or mediates the hydrolysis, alcoholysis, or aminolysis of racemic amides or carbamates. Each method provides a mixture of the amine enantiomer along with the opposite enantiomer of the amide or carbamate. Separation of the enantiomers and subsequent cleavage of the amide or carbamate provides both enantiomers. The fused bicyclic ring system comprises an optionally-substituted 5- or 6-membered heteroaromatic ring (ring C) fused to an optionally-substituted 5- or 6-membered partially or fully saturated cycloalkyl or heterocycloalkyl (ring D).

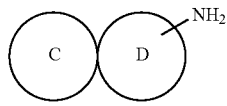

XI

The heteroaromatic ring includes: pyridine, pyrimidine, pyrazine, pyridazine, triazine, imidazole, pyrazole, triazole, oxazole and thiazole. The saturated ring includes cyclohexane, piperidine, piperazine, hexahydropyridazine, tetrahydrofuran, tetrahydrothiophene, tetrahydropyran and tetrahydrothiapyran.

This invention provides a process for resolving racemic amino-substituted 5,6,7,8-tetrahydroquinoline of the formula V or racemic amino-substituted 5,6,7,8-tetrahydroisoquinoline of the formula VI to produce the two enantiomers:

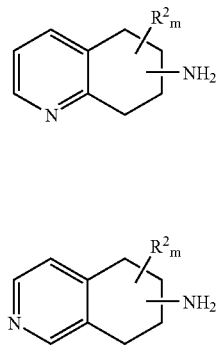

comprising:

a) enantioselectively acylating or carbamoylating the racemic amino-substituted 5,6,7,8-tetrahydroquinoline or the racemic amino-substituted 5,6,7,8-tetrahydroisoquinoline using an enantioselective enzyme as a catalyst; and b) separating the unreacted amino-substituted 5,6,7,8-tetrahydroquinoline or 5,6,7,8-tetrahydroisoquinoline as the first enantiomer, from the enantiomeric amide- or carbamate-substituted 5,6,7,8-tetrahydroquinoline or 5,6,7,8-tetrahydroisoquinoline; and c) cleaving the amide or carbamate group to isolate the second enantiomer of the amino-substituted 5,6,7,8-tetrahydroquinoline or 5,6,7,8-tetrahydroisoquinoline;

wherein $NH_2$ is located at any position on the saturated portion of the quinoline or isoquinoline; $R^2$ is located at any other hydrogen position on the quinoline or isoquinoline ring; m is 0–4; and $R^2$ is selected from the group consisting of halo, nitro, cyano, carboxylic acid, alkyl, alkenyl, cycloalkyl, hydroxyl, thio, a protected amino, acyl, carboxylate, carboxamide, sulfonamide, an aromatic group and a heterocyclic group.

A preferred method also is described for using an enzyme to resolve the enantiomers of 8-amino-5,6,7,8-tetrahydroquinoline (Scheme 3). An enzyme may be used to catalyze the process in which a single enantiomer of a racemic mixture of 8-amino-5,6,7,8-tetrahydroquinoline reacts with a suitable ester, carboxylic acid or carbonate to give a mixture of either the corresponding amide or carbamate, respectively, and the unreacted amine in enantiopure form (equations 1 and 2). This method may be used to prepare either enantiomer of 8-amino-5,6,7,8-tetrahydroquinoline, either by isolation of the resolved amine or by cleavage of the amide or carbamate group in the resolved, protected material.

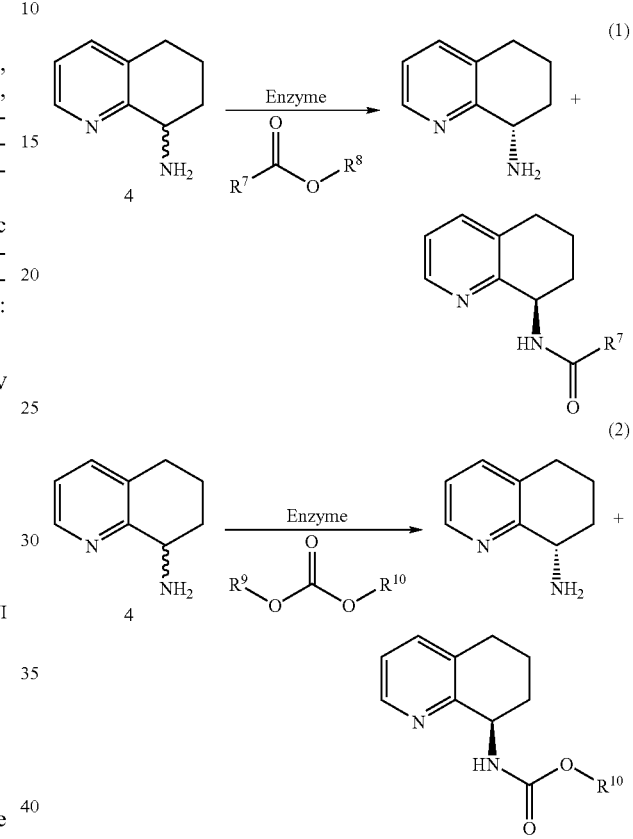

For the esters, R7 is selected from the group consisting of H, lower alkyl (C1 through C12), alkenyl, alkynyl, aryl, heteroaryl, substituted aryl, substituted heteroaryl, cycloalkyl, cycloalkenyl, carbocyclic, heterocyclic, benzyl, vinyl, and allyl; R8 is selected from the group consisting of H, lower alkyl (C1 through C12), vinyl, benzyl, allyl, trifluoroethyl, alkenyl, alkynyl, aryl, heteroaryl, substituted aryl, substituted heteroaryl, cycloalkyl, cycloalkenyl, carbocyclic, and heterocyclic. For the carbamates, R9 and R10 are the same or different and are selected from the group consisting of lower alkyl (C1 through C12), vinyl, allyl, benzyl, trifluoroethyl, alkenyl, alkynyl, aryl, heteroaryl, substituted aryl, substituted heteroaryl, cycloalkyl, cycloalkenyl, carbocyclic, and heterocyclic.

Another process is provided for resolving racemic amino-substituted 5,6,7,8-tetrahydroquinoline or racemic amino-substituted 5,6,7,8-tetrahydroisoquinoline to produce the two enantiomers, comprising:

a) reacting racemic amide- or carbamate-substituted 5,6,7,8-tetrahydroquinoline of the formula VII or racemic amide- or carbamate-substituted 5,6,7,8-tetrahydroisoquinoline of the formula VIII

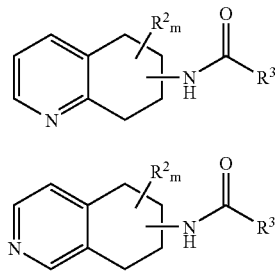

with water, an alcohol, or a primary or secondary amine using an enantioselective enzyme as a catalyst to produce a mixture of the corresponding amino in the first enantiomeric form, and the unreacted amide or carbamate in the second enantiomeric form;

b) separating the first enantiomer of the amino-substituted 5,6,7,8-tetrahydroquinoline or amino-substituted 5,6,7,8-tetrahydroisoquinoline, from the unreacted amide or carbamate; and c) cleaving the amide or carbamate group to produce the second enantiomer of the amino-substituted 5,6,7,8-tetrahydroquinoline or amino-substituted 5,6,7,8-isoquinoline;

wherein the amide or carbamate group is located at any position on the saturated portion of the quinoline or isoquinoline; $R^2$ is located at any other hydrogen position on the quinoline or isoquinoline ring; m is 0–4; $R^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and $R^3$ is an optionally substituted carbon atom or an optionally substituted oxygen atom.

Alternatively, an enzyme may be used to catalyze the process in which a racemic mixture of a suitable amide or carbamate derived from 8-amino-5,6,7,8-tetrahydroquinoline undergoes enantioselective hydrolysis to give a single enantiomer of 8-amino-5,6,7,8-tetrahydroquinoline and the parent amide or carbamate in enantiopure form (equations 3 and 4). This method may be used to prepare either enantiomer of 8-amino-5,6,7,8-tetrahydroquinoline, either by isolation of the resolved hydrolyzed amine or by cleavage of the amide or carbamate group in the resolved, protected material.

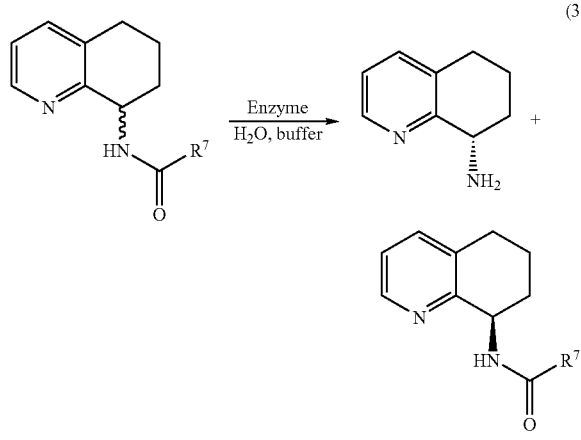

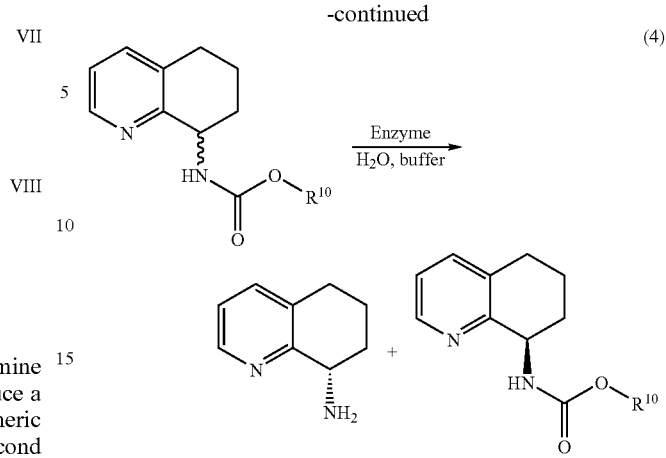

Suitable enzymes for the above processes include (but are not limited to) the following:

Lipases:
*Candida antarctica* (A and B)
*Candida rugosa* (also called *Candida cylindracea*)
*Pseudomonas fluorescens* (also called *Pseudomonas cepacia*; same as *Burkholderia cepacia*)
*Pseudomonas aeruginosa*
*Alcaligenes* sp. lipase
*Burkholderia plantarii* (*Pseudomonas plantarii*)
*Pseudomonas* sp. lipase
*Chromobacterium viscosum* lipase (*Burkholderia glumae*)
Porcine pancreatic lipase
*Mucor* sp. (*Mucor miehei* lipase)
*Rhizopus delemar* lipase
*Rhizomucor miehei* lipase
*Rhizopus niveus* and
*Humicola lanuginosa*;

Proteases:
Substilin Carlsberg and
Substilin BPN'; and
Penicillin acylase from *Alcaligenes faecalis*.

The use of certain enzymes to resolve selected racemic amines (or to selectively hydrolyze racemic amides) is described. See:

1. Reetz, M. T.; Driesbach, C. *Chimia*, 1994, 48, 570;
2. Iglesias, L. E.; Sanchez, V. M.; Rebolledo, F.; Gotor, V. *Tetrahedron: Asymmetry*, 1997, 8, 2675;
3. Takayama, S.; Lee, S. T.; Hung, S.-C.; Wong, C.-H. *Chem. Commun.*, 1999, 2, 127;
4. Smidt, H.; Fisher, A.; Fisher, P.; Schmid, R. D. *Biotechnol. Tech.*, 1996, 10, 335;
5. Koeller K. M., Wong C. H. *Nature*, 2001, 409, 232;
6. Carrea G., Riva S. *Angew. Chem. Int. Ed. Engl.* 2000, 39, 2226;
7. vanRantwijk F., Hacking M. A. P. J., Sheldon R. A. *Monat. Chem.* 2000, 131, 549;
8. Hacking M. A. P. J., vanRantwijk F., Sheldon R. A. *J. of Molecular Catalysis B:Enzymatic.* 2000, 9, 201;
9. Gotor V. *Biocat. Biotrans.* 2000, 18, 87;
10. Morgan B., Zaks A., Dodds D. R., Liu J. C., Jain R., Megati S., Njoroge F. G., Girijavallabhan V. M. *J. Org. Chem.* 2000, 65, 5451;
11. Kazlauskas, R. J.; Weissfloch, A. N. E.; *J. of Molecular Catalysis B:Enzymatic* 1997, 3, 65–72;
12. Sanchez, V. M.; Rebolledo, F.; Gotor, V. *Tet. Asym.* 1997, 8, 37–40.

13. Wagegg, T.; Enzelberger, M. M.; Bornscheuer, U. T.; Schmid, R. D. *Journal of Biotechnology*, 1998, 61, 75–78;
14. Messina, F.; Botta, M.; Corelli, F.; Schneider, M. P.; Fazio, F. *J. Org. Chem.* 1999, 64, 3767–3769;
15. Soledad de Castro, M.; Dominguez, P.; Sinisterra, J. V. *Tetrahedron* 2000, 56, 1387–1391;
16. Maestro, A.; Astrorga, C.; Gotor, V. *Tet. Asym.* 1997, 8, 3153–3159;
17. Balkenhohl, F.; Ditrich, K.; Hauer, B.; Ladner, W. *J. Prakt. Chem.* 1997, 339, 381–384;
18. Luna, A.; Astorga, C.; Fulop, F.; Gotor, V. *Tet. Asym.* 1998, 9, 4483–4487;
19. Van Langen, L. M.; Oosthoek, N. H. P.; Guranda, D. T.; Van Rantwijk, F.; Svedas, V. K.; Sheldon, R. A. *Tet. Asym.* 2000, 11, 4593–4600; and
20. Ami, E.; Horui, H. *Biosci. Biotechnol. Biochem.* 1999, 63, 2150–2156.

The enzymatic processes are preferably conducted utilizing a lipase or protease as the enantioselective enzyme and are more preferably selected from the group consisting of *Candida antarctica* A and B, *Candida rugosa*, *Pseudomonas fluorescens*, Substilin Carlsberg, Substilin BPN' and *Alcaligenes faecalis* penicillin.

The acylating agent is either an optionally substituted acid, an optionally substituted ester or an optionally substituted primary, secondary, or tertiary amide. The carbarmoylating agent is an optionally substituted carbonate. Preferably, the acylating agent is ethyl acetate and the carbamoylating agent is dibenzyl carbonate or a dialkyl carbonate.

The enzymatic resolution is preferably carried out in a solvent or combination of solvents such as: etheral solvents (e.g. diethyl ether, diisopropyl ether, dibutyl ether, methyl tert-butyl ether, dipentyl ether, tert-amyl methyl ether, dimethoxy ethane, 2-methoxyethyl ether, diethylene glycol dimethyl ether (diglyme), diphenyl ether, dibenzyl ether, tetrahydrofuran, 1,4-dioxane, morpholine, etc.), aromatic solvents (e.g. benzene, toluene, ethylbenzene, o-xylene, m-xylene, p-xylene, xylenes, mesitylene, nitrobenzene, chlorobenzene, o-dichlorobenzene, p-dichlorobenzene, 1,2,4-trichlorobenzene, naphthalene, pyridine, 1-methylpyrrole, furan, thiophene, etc.), chlorinated alkyl solvents (e.g. methylene chloride, chloroform, dichloroethane, trichloroethylene, etc.), dipolar aprotic solvents (e.g. carbon disulfide, dimethylformamide, dimethyl sulfoxide, 1-methyl-2-pyrrolidinone, acetonitrile, nitromethane, nitroethane, etc.), alkane solvents (e.g. petroleum ether, mineral spirits (ligroin), pentane, hexane, hexanes, heptane, octane, isooctane, nonane, decane, hexadecane, 2-methylbutane, cyclopentane, cyclohexane, etc.), alkene solvents (e.g. 1-pentene, 1-hexene, cyclopentene, cyclohexene, etc.), ketone solvents (e.g. acetone, butanone, 2-pentanone, 3-pentanone, methyl isobutyl ketone, cyclopentanone, cyclohexanone, cycloheptanone, etc.), water. The enzymatic acylation or carbamoylation is preferably carried out in either diisopropyl ether or methyl tert-butyl ether, although in these cases the acylating agent or the carbamoylating agent may also be used as solvent. The preferred acylating agent in this case is ethyl acetate, while the preferred carbamoylating agents are dibenzyl carbonate and diallyl carbonate. The preferred solvent for the enzymatic hydrolysis, alcoholysis and aminolysis is water, although in these cases the alcohol or amine nucleophile may also be used as solvent.

The reaction temperature is between about 0° C. to about 120° C. with the preferred temperature from about 50 to about 60° C.

The concentration for the enzymatic resolution is from about 0.01M to about 10M with respect to the starting substrate, with the preferred concentration being from about 0.3 to about 0.6M, whereas the number of equivalent enzyme to substrate is about 0.01 to about 10 by weight, with the preferred equivalent being from about 0.3 to about 0.4 equivalents by weight. Typically, the reaction time is from about 30 minutes to about 48 hours, preferably from about 2 hours to about 6 hours.

The amide or carbamate substituted compounds are hydrolyzed using standard conditions, such as hydrochloric acid in acetone under reflux conditions or hydrochloric acid under reflux conditions. Preferably, the amino group is located at the 8-position of a 5,6,7,8-tetrahydroquinoline or at the 5-position of a 5,6,7,8-tetrahydroisoquinoline, m is 0 or 1, and $R^2$ is methyl.

Racemization Process

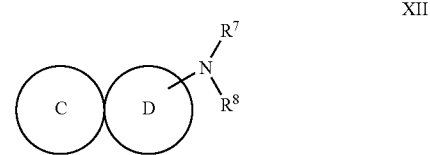

XII

This invention provides a procedure to racemize the single enantiomers of optionally substituted amino-substituted fused bicyclic ring systems XII, wherein treatment of the enantiomerically pure or enantiomerically enriched amine, either as the primary, secondary or tertiary amine, or as an amine derivative, under the proscribed experimental conditions converts it to the racemate. In cases where the amine is substituted as an amine derivative (such as an amide, carbamate, or urea), hydrolysis of this functional group under acidic or basic conditions subsequent to the racemization procedure affords the corresponding racemic amine. The fused bicyclic ring system comprises an optionally-substituted 5- or 6-membered heteroaromatic ring (ring C) fused to an optionally-substituted 5- or 6-membered partially or fully saturated cycloalkyl or heterocycloalkyl (ring D). The heteroaromatic ring includes: pyridine, pyrimidine, pyrazine, pyridazine, triazine, imidazole, pyrazole, triazole, oxazole and thiazole. The saturated ring includes cyclohexane, piperidine, piperazine, hexahydropyridazine, tetrahydrofuran, tetrahydrothiophene, tetrahydropyran and tetrahydrothiapyran. The optional substituents on the amino group ($R^7$ and $R^8$ above) include: hydrogen, optionally substituted alkyl, aryl, heteroalkyl, heteroaryl, aralkyl, alkanoyl, alkylsulfonyl, a carbonyl or group substituted by an aromatic or heterocyclic ring, aryloxycarbonyl, alkoxycarbonyl, arylcarbamoyl, alkylcarbamoyl, arylthiocarbonyl, alkylthiocarbonyl, and carbamoyl.

This invention provides a process for racemizing a single enantiomer of amino-substituted 5,6,7,8-tetrahydroquinoline of the formula XIII or of amino-substituted 5,6,7,8-tetrahydroisoquinoline of the formula XIV to produce the corresponding racemic mixture:

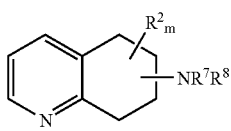

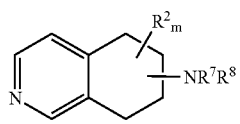

comprising:

a) heating an enantiomerically enriched amino-substituted 5,6,7,8-tetrahydroquinoline or an enantiomerically enriched amino-substituted 5,6,7,8-tetrahydroisoquinoline neat or in an organic solvent in the presence or absence of an additive; and b) when either $R^7$ or $R^8$ is not hydrogen, cleaving the $R^7$ or $R^8$ groups under conditions (e.g. acid-promoted hydrolysis in the case of amides and carbamates) to afford the corresponding racemic amine, wherein $NR^7R^8$ is located at any position on the saturated portion of the quinoline or isoquinoline; $R^2$ is located at any other hydrogen position on the quinoline or isoquinoline ring; m is 0–4; and $R^2$ is selected from the group consisting of halo, nitro, cyano, carboxylic acid, alkyl, alkenyl, cycloalkyl, hydroxyl, thio, a protected amino, acyl, carboxylate, carboxamide, sulfonamide, an aromatic group and a heterocyclic group.

A preferred method also is described for racemization of enantioenriched (R)— or (S)— 8-amino-5,6,7,8-tetrahydroquinoline or enantioenriched (R)— or (S)—N-(5,6,7,8-tetrahydro-quinolin-8-yl)-amides and carbamates (Scheme 4). This method may be used to racemize either enantiomer of 8-amino-5,6,7,8-tetrahydroquinoline or its corresponding amides or carbamates. In the case of the amides and carbamates, the amide and carbamate groups may be cleaved to afford the corresponding amine. In either case, the racemic amine thus obtained may be resubmitted to the Enzymatic Resolution Process described above and thereby recycled.

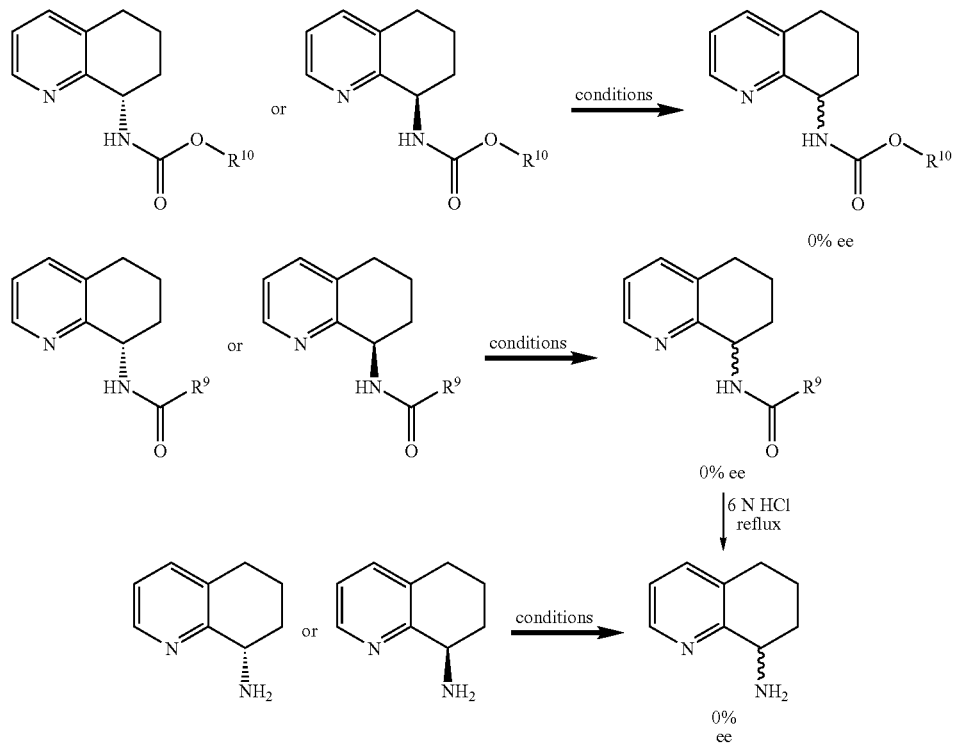

For the amides, $R^9$ is selected from the group consisting of H, $C_1$–$C_{12}$ alkyl, alkenyl, alkynyl, aryl, heteroaryl, substituted aryl, substituted heteroaryl, cycloalkyl, cycloalkenyl, carbocyclic, heterocyclic, benzyl, vinyl, and allyl. For the carbamates, $R^{10}$ is selected from the group consisting of $C_1$–$C_{12}$ alkyl, vinyl, allyl, benzyl, trifluoroethyl, alkenyl, alkynyl, aryl, heteroaryl, substituted aryl, substituted heteroaryl, cycloalkyl, cycloalkenyl, carbocyclic, and heterocyclic.

The racemization reaction is preferably carried out neat or in a solvent, or combination of solvents such as: etheral solvents (e.g. diethyl ether, diisopropyl ether, dibutyl ether, methyl tert-butyl ether, dipentyl ether, tert-amyl methyl ether, dimethoxy ethane, 2-methoxyethyl ether, diethylene glycol dimethyl ether (diglyme), diphenyl ether, dibenzyl ether, tetrahydrofuran, 1,4-dioxane, morpholine, etc.), aromatic solvents (e.g. benzene, toluene, ethylbenzene, o-xylene, m-xylene, p-xylene, xylenes, mesitylene, nitrobenzene, chlorobenzene, o-dichlorobenzene, p-dichlorobenzene, 1,2,4-trichlorobenzene, naphthalene, pyridine, 1-methylpyrrole, furan, thiophene, etc.), chlorinated alkyl solvents (e.g. methylene chloride, chloroform, dichloroethane, trichloroethylene, etc.), dipolar aprotic solvents (e.g. carbon disulfide, dimethylformamide, dimethyl sulfoxide, 1-methyl-2-pyrrolidinone, acetonitrile, nitromethane, nitroethane, etc.), alkane solvents (e.g. petroleum ether, mineral spirits (ligroin), pentane, hexane, hexanes, heptane, octane, isooctane, nonane, decane, hexadecane, 2-methylbutane, cyclopentane, cyclohexane, etc.), alkene solvents (e.g. 1-pentene, 1-hexene, cyclopentene, cyclohexene, etc.), ketone solvents (e.g. acetone, butanone, 2-pentanone, 3-pentanone, methyl isobutyl ketone, cyclopentanone, cyclohexanone, cycloheptanone, etc.), or water. The racemization of the unsubstituted primary amine or the corresponding amide or carbamate is most preferably carried out neat (in the absence of solvent).

The reaction temperature is between about 0° C. to about 300° C. with the preferred temperature from about 120° C. to about 150° C.

For the cases where a solvent is employed, the concentration for the racemization is from about 0.01M to about 10M with respect to the starting substrate, with the preferred concentration being from about 0.3 to about 0.6M.

The racemization reaction optionally may be carried out in the presence of either a catalytic or stoichiometric amount of an appropriate additive or combination of additives, such as a base, a Lewis acid, an aldehyde or a ketone. Suitable bases include: lithium, sodium, potassium or cesium hydroxide bases (KOH, NaOH, LiOH, CsOH), lithium, sodium, potassium or cesium alkoxide bases (sodium methoxide, sodium ethoxide, sodium isopropoxide, sodium tert-butoxide, potassium tert-butoxide, lithium methoxide), lithium, sodium, potassium hydride bases (LiH, NaH, KH), alkyllithium bases (methyllithium, n-butyllithium, s-butyllithium, tert-butyllithium, isobutyllithium, phenyllithium, ethyllithium, n-hexyllithium, or isopropyllithium), or lithium, sodium, or potassium amide bases (lithium amide, sodium amide, potassium amide, lithium hexamethyldisilazide, sodium hexamethyldisilazide, potassium hexamethyldisilazide, lithium diisopropylamide, lithium diethylamide, lithium dicyclohexylamide, or lithium 2,2,6,6-tetramethylpiperidide) or any appropriate combination thereof. Suitable Lewis acids include: metal salts ($AlCl_3$, $FeCl_3$, $CrCl_2$, $HgCl_2$, $CuCl$, $TiCl_4$, $Yb(OTf)_3$, InOTf, $TiCl_2O^iPr_2$, $Ti(O^iPr)_4$), organometallic species (trimethylaluminum, dimethylaluminum chloride), and boron species ($BF_3$, $B(OMe_3)$, $B(O^iPr)_3$). Suitable aldehydes include: benzaldehyde, 4-methoxybenzaldehyde, 2,6-dichlorobenzaldehyde, acetaldehyde, and formaldehyde. Suitable ketones include: acetone, acetophenone, butanone, 2-pentanone and cyclohexanone. The preferred amount of the additive, in terms of the number of equivalents additive to substrate, is about 0.01 to about 10 by weight, with the preferred equivalent being from about 0.1 to about 1 equivalents by weight. The racemization of the unsubstituted primary amine or the corresponding amide or carbamate is preferably carried out in the absence of an additive.

Typically, the reaction time is from about 30 minutes to about 48 hours, preferably from about 1 hour to about 2 hours.

The racemization is preferably carried out in the presence of an inert atmosphere, most preferably under an atmosphere of dry nitrogen or argon.

The racemic amide or carbamate substituted compounds are hydrolyzed using standard conditions, such as hydrochloric acid in acetone under reflux conditions or hydrochloric acid under reflux conditions. Preferably, the amino group is located at the 8-position of a 5,6,7,8-tetrahydroquinoline or at the 5-position of a 5,6,7,8-tetrahydroisoquinoline, m is 0 or 1, $R^9$ is methyl, and $R^{10}$ is methyl, allyl, or benzyl.

Asymmetric Synthesis Process

The invention also describes a process for the formation of a stereodefined amino group by forming an imine between an enantiomerically pure primary amine chiral auxiliary group and a ketone substrate followed by diastereoselective reduction of the resulting imine to provide a secondary amine, and then removal of the chiral auxiliary to produce an enantiomer of the primary amino group on the substrate. Either enantiomeric form of the primary amine can be prepared. Alternatively, in a prestep, the ketone is formed by oxidizing a corresponding hydroxyl group under standard conditions.

A process is provided for synthesizing an enantiomer of a primary amino-substituted fused bicyclic ring of formula IX comprising:

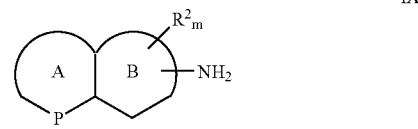

IX a) forming the Schiff base of a keto group located on ring B of the fused bicyclic ring by reacting it with an enantiomerically-pure primary amine chiral auxiliary $R^*NH_2$ of the formula X

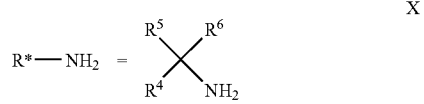

X to produce the corresponding enantiomerically-pure imine of the fused bicyclic ring;

b) diastereoselectively reducing the imine to produce the corresponding enantiomerically-pure secondary amine on the fused bicyclic ring; and c) removing the chiral auxiliary $R^*$ to form the enantiomer of the primary amino-substituted fused bicyclic ring;

wherein ring A is a heteroaromatic 5- or 6-membered ring, P is a nitrogen atom, sulfur atom or oxygen atom; ring B is a 5- or 6-membered partially or fully saturated cycloalkyl or heterocycloalkyl;

wherein $NH_2$ is located at a position on ring B; and $R^2$ is located at any other hydrogen position on the fused bicyclic ring;

wherein m is 0–4; $R^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and $R^4$, $R^5$, and $R^6$ are each different and selected from the group consisting of hydrogen, alkyl, alkenyl, cycloalkyl, cycloalkenyl, and a 5- or 6-membered aromatic ring; and at least one of $R^4$, $R^5$, or $R^6$ is a 5- or 6-membered aromatic or heteroaromatic ring.

A preferred process for the synthesis of enantiomerically enriched 8-amino-5,6,7,8-tetrahydroquinoline using a chiral auxiliary is described (Scheme 5). The protocol involves formation of the Schiff base of 6,7-dihydro-5H-quinolin-8-one 10 with an appropriate enantiomerically pure primary benzylic amine (R*—$NH_2$) to give the imine 11. Subsequent reduction of 11 with a suitable hydride reagent (e.g. sodium borohydride) followed by reductive cleavage of the chiral auxiliary provides the title compound 8 in enantiomerically pure (or enantiomerically enriched) form. This synthetic route may be adapted to prepare either enantiomer of 8 depending on the choice of chiral auxiliary.

$C_{12}$), alkenyl, alkynyl, aryl, heteroaryl, substituted aryl, substituted heteroaryl, cycloalkyl, cycloalkenyl, carbocyclic, heterocyclic, carboxylate, amide, carboxylic acid, and benzyl.

Examples of suitable chiral auxiliaries include (but are not limited to) the following:

(R) or (S)-1-phenylethylamine,
(R) or (S)-1-(1-naphthyl)ethylamine,
(R) or (S)-1-(2-naphthyl)ethylamine,
(R) or (S)-2-phenylglycinol,
(R) or (S)-(4-bromophenyl)ethylamine,
(R) or (S)-alpha-methyl-4-nitrobenzylamine,
(1S,2R) or (1R,2S)-2-amino-1,2-diphenylethanol,
(R) or (S)-1-phenylpropylamine,
(R) or (S)-1-(P-tolyl)ethylamine,
(1S,2R) or (1R,2S)-cis-1-amino-2-indanol,
(R) or (S)-1-aminoindan,
(R) or (S)-1-phenyl-2-(p-tolyl)ethylamine,
(R) or (S)-1-aminotetralin,
(R) or (S)-3-bromo-alpha-methylbenzylamine,
(R) or (S)-4-chloro-alpha-methylbenzylamine,
(R) or (S)-3-methoxy-alpha-methylbenzylamine,
(R) or (S)-2-methoxy-alpha-methylbenzylamine,
(R) or (S)-4-methoxy-alpha-methylbenzylamine,
(R) or (S)-3-amino-3-phenyl propan-1-ol, and
(R) or (S)-1-amino-1-phenyl-2-methoxyethane.

The chiral auxiliary compound is preferably phenylethylamine, naphthylethylamine, phenylpropylamine, or meth-

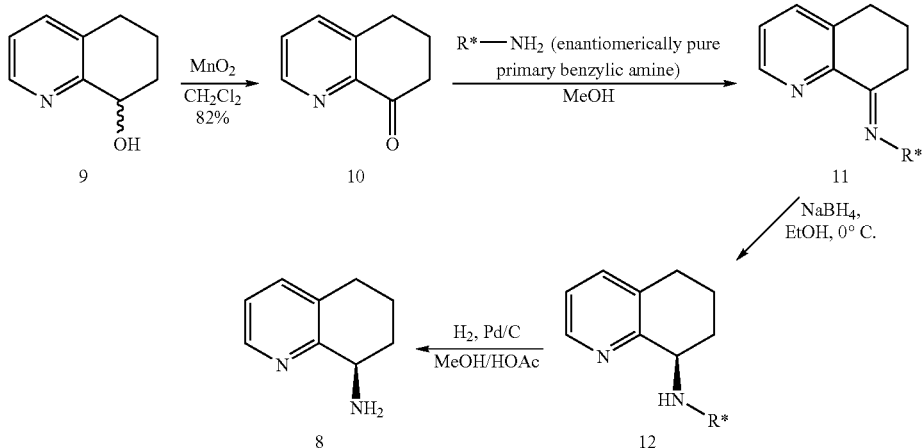

Scheme 5

Suitable chiral auxiliaries to be used in this sequence are of general formula X, in which $R^4$, $R^5$, and $R^6$ are non-equivalent. At least one of $R^4$–$R^6$ must be an aromatic group (either a 5- or 6-membered aryl, heteroaryl, substituted aryl, or substituted heteroaryl); otherwise, $R^4$–$R^6$ may be composed from the list shown below:

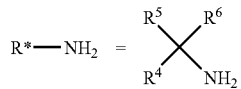

Wherein $R^4$, $R^5$, and $R^6$ are the same or different and are selected from the group consisting of H, alkyl ($C_1$ through oxyphenylethylamine, more preferably (R)-(+)-phenylethylamine, (R)-(+)-1-phenylpropylamine, or (S)-(−)-1-(4-methoxyphenyl)ethylamine.

Suitable solvents for the formation of the imine and/or reduction of the imine to the amine include, alone or in combination,: ethereal solvents (diethyl ether, diisopropyl ether, dibutyl ether, methyl tert-butyl ether, dipentyl ether, tert-amyl methyl ether, dimethoxy ethane, 2-methoxyethyl ether, diethylene glycol dimethyl ether, diphenyl ether, dibenzyl ether, tetrahydrofuran, 1,4-dioxane, or morpholine), aromatic solvents (benzene, toluene, ethylbenzene, o-xylene, m-xylene, p-xylene, mesitylene, nitrobenzene, chlorobenzene, o-dichlorobenzene, p-dichlorobenzene, 1,2,4-trichloroenzene, naphthalene, pyridine, 1-methylpyrrole, furan, or thiophene), chlorinated alkyl solvents (methylene chloride, chloroform, dichloroethane, thrichloroethane), alkane solvents (petroleum ether, mineral spirits, pentane, hexane, heptane, octane, isooctane, nonane, decane, hexadecane, 2-methylbutane, cyclopentane, or cylohexane), and alcohol solvents (methanol, ethanol, propanol, isopropanol, n-butanol, isobutanol, s-butanol, pentanol, isoamyl alcohol, or cyclohexanol). Preferred solvents are chlorinated alkyl solvents, such as methylene chloride, and alcohol solvents, such as methanol and ethanol.

Reducing agents include: boron-based hydride reducing agents (sodium borohydride, lithium borohydride, potassium borohydride, sodium cyanoborohydride, sodium triacetoxyborohydride, lithium tri-sec-butylborohydride, lithium triethylborohydride, lithium trisiamylborohydride, catechol borane, 9-BBN, disiamyl borane, thexyl borane, or borane), aluminum-based hydride reagents (diisobutylaluminum hydride, lithium aluminum hydride, or sodium bis(2-methoxyethoxy)aluminum hydride), and hydrogen gas in combination with an appropriate metal catalyst (palladium on carbon, platinum oxide, Raney-nickel, rhodium on carbon, or ruthenium on carbon).

The number of equivalents of reducing agent is between about 0.2 and about 10 equivalents, with preferably about 1 to about 2 equivalents. The concentration is about 0.01M to about 10M with respect to the starting substrate, with preferably from about 0.2 to about 0.6M, whereas the temperature of the reaction is from about −100 to about 100° C., most preferably from about −30 to about 25° C.

The stoichometry between the starting bicyclic ring and the chiral auxiliary compound is about 1:0.5 to about 1:5, with 1:1 being preferred.

Removal of the chiral auxiliary is accomplished via standard methods, such as hydrogenation in an appropriate solvent or in the presence of a metal catalyst, or acid-mediated cleavage.

Preferably, the fused bicyclic ring is an amino-substituted 5,6,7,8-tetrahydroquinoline or 5,6,7,8-tetrahydroisoquinoline, m is 0 or 1, and $R^2$ is methyl.

Also provided by this invention are novel intermediate compounds as shown in the examples. Most preferred are those that are enantiomeric.

The following examples are intended to illustrate, but not to limit, the invention.

EXAMPLES

Preparation of (R,S)-8-Amino-5,6,7,8-tetrahydroquinoline by Selective Hydrogenation of N-(Quinolin-8-yl)-acetamide

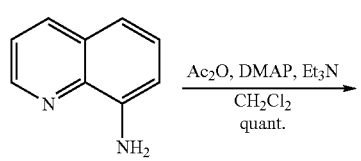

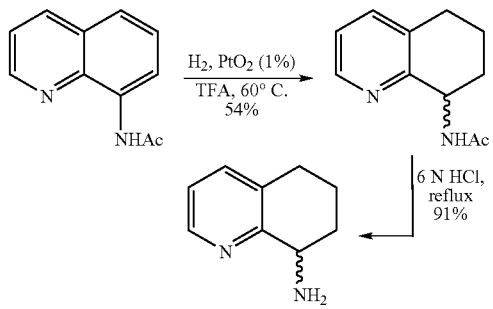

Preparation of N-(Quinolin-8-yl)-acetamide

To a stirred solution of 8-aminoquinoline (33.37 g, 0.231 mol), DMAP (4-dimethylaminopyridine) (1.40 g, 0.011 mol) and triethylamine ($Et_3N$) (37 mL, 0.265 mol) in $CH_2Cl_2$ (methylene chloride) (275 mL) was added acetic anhydride ($Ac_2O$) (26.5 mL, 0.281 mol). After 20 hours the reaction mixture was poured into a saturated aqueous solution of $NaHCO_3$ (sodium bicarbonate). The phases were separated and the aqueous phase was extracted with ether (3×150 mL). The combined organic phases were dried ($Na_2SO_4$) (sodium sulfate), filtered and concentrated in vacuo to provide 43.56 g (100%) of N-(quinolin-8-yl)-acetamide as a beige solid. This material was used without further purification in subsequent steps. $^1$H NMR ($CDCl_3$) δ 2.35 (s, 3H), 7.42–7.56 (m, 3H), 8.15 (dd, 1H, J=1.5, 8.4 Hz), 8.76 (dd, 1H, J=1.8, 7.2 Hz), 8.79 (dd, 1H, J=1.5, 4.2 Hz), 9.78 (br s, 1H); $^{13}$C NMR ($CDCl_3$) δ 25.5, 116.8, 121.8, 122.0, 127.8, 128.3, 134.9, 136.8, 138.6, 148.5, 169.2. ES-MS m/z 187 (M+H).

Preparation of (R,S)-N-(5,6,7,8-Tetrahydroquinolin-8-yl)-acetamide

N-(Quinolin-8-yl)-acetamide (173.27 g, 0.930 mol) was dissolved in trifluoroacetic acid (TFA) (2.7 L) in a 10 L three-neck round bottom flask equipped with Teflon tubing for gas addition, temperature control probe and an overhead mechanical stirrer. The vigorously stirred solution was warmed to 60° C. and degassed for 20 minutes with nitrogen gas. Platinum oxide ($PtO_2$) (2.11 g, 9.3 mmol) was added as a solid. Hydrogen gas ($H_2$) was then slowly bubbled from the tank through the solution. The reaction was complete after 5.5 h as determined by GC (gas chromatography) analysis of an aliquot of the reaction mixture. The reaction mixture was then degassed with nitrogen and cooled to 30° C. It was filtered though a glass frit to remove the catalyst and the solvent was removed in vacuo. The resulting material was treated with saturated aqueous NaOH (sodium hydroxide) solution until the solution reached pH 14. The solution was extracted with $CH_2Cl_2$ (8×500 mL), dried magnesium sulfate ($MgSO_4$), filtered and concentrated in vacuo. The crude material was purified by flash column chromatography on silica gel (elution with 1% MeOH (methanol) in $CH_2Cl_2$, then 5% MeOH (methanol) in $CH_2Cl_2$) to provide 95.37 g (54%) of (R,S)—N-(5,6,7,8-tetrahydroquinolin-8-yl)-acetamide. $^1$H NMR ($CDCl_3$): δ 1.80–2.00 (m, 4H), 2.79–2.85 (m, 2H), 2.90–3.00 (m, 2H), 3.91 (s, 3H), 7.95 (s, 1H), 8.93 (s, 1H); $^{13}$C NMR ($CDCl_3$) δ 22.8, 23.1, 28.9, 30.0, 33.1, 52.5, 123.7, 132.5, 138.0, 148.2, 162.6, 166.5. ES-MS m/z 192 (M+H).

Preparation of (R,S)-8-Amino-5,6,7,8-tetrahydroquinoline

8-Acetamido-5,6,7,8-tetrahydroquinoline (41.94 g, 0.220 mol) was dissolved in 6 N HCl (hydrochloric acid) (550 mL) and was heated to reflux. After 17 hours the reaction mixture was cooled to room temperature and was treated with saturated aqueous NaOH solution until it reached pH 14. The mixture was then extracted with $CH_2Cl_2$ (4×500 mL), and the combined organic extracts were dried ($MgSO_4$), filtered and concentrated in vacuo. The resulting crude material was purified by Kugelrohr distillation to provide 29.62 g (91%) of (R,S)-8 amino-5,6,7,8-tetrahydroquinoline as a colorless oil. $^1$H NMR ($CDCl_3$) δ 1.52–1.62 (m, 2H), 1.78–1.85 (m, 1H), 1.91 (br s, 2H), 2.02–2.06 (m, 1H), 2.60–2.65 (m, 2H), 3.83–3.87 (m, 2H), 6.91 (dd, 1H, J=8, 5 Hz), 7.21 (dd, 1H, J=8, 1 Hz), 8.26 (d, 1H, J=5 Hz); $^{13}$C NMR ($CDCl_3$) δ 19.6, 28.7, 31.7, 51.0, 121.3, 131.2, 136.4, 146.7, 159.2. ES-MS m/z 149 (M+H).

Additional examples of the selective hydrogenation are provided in the table below and in equation 6.

TABLE 1

Hydrogenation of substituted quinolines 1a-m (Equation 5)[a]

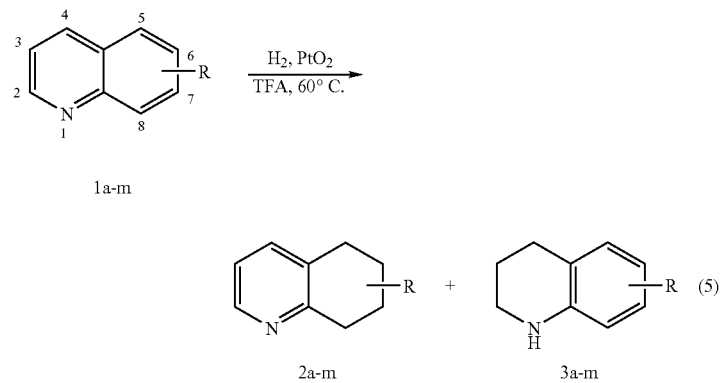

| Entry | Compound | R | Reaction Time (h) | Yield of 2 (%) | Yield of 3 (%) |
|---|---|---|---|---|---|
| 1 | 1a | 2-NHAc | 18 | 69 | 0 |
| 2 | 1b | 3-NHAc | 3.5 | 63 | 1 |
| 3 | 1c | 4-NHAc, 2-Me | 20 | 78 | 0 |
| 4 | 1d | 5-NHAc | 4.5 | 45 | 27 |
| 5 | 1e | 6-NHAc | 5 | 49 | 28 |
| 6 | 1f | 7-NHAc | 18 | 25 | 20 |
| 7 | 1g | 8-NHAc | 2.5 | 52 | 15 |
| 8 | 1h | 8-NHAc, 2-Me | 3 | 57 | 15 |
| 9 | 1i | 3-MeO | 4 | 65 | 0c |
| 10 | 1j | 2-Ph | 5 | 68 | 10 |
| 11 | 1k | 2-COOMe | 4 | 51 | 20 |
| 12 | 1l | 3-COOMe | 5 | 70 | 11 |

TABLE 1-continued

| 13 | 1m | 6-COOMe | 5 | 30 | 39 |
| 14 | 1n | 8-COOMe | 2 | 36 | 28d |

[a]Unless otherwise noted, all reactions were performed with 0.3 M substrate in TFA using 5 mol % PtO$_2$ at 60° C. under 1 atm hydrogen. The progress of each reaction was monitored by GC and/or TLC. Yields are for isolated, purified product.
[b]Yields are approximate as the reaction was performed on a small scale (30 mg 1f) with 20% PtO$_2$.
[c]Trace amounts (~2%) of hydrogenolyzed products were detected (quinoline, 1,2,3,4-THQ, 5,6,7,8-THQ).
[d]16% of the starting material remained unreacted.

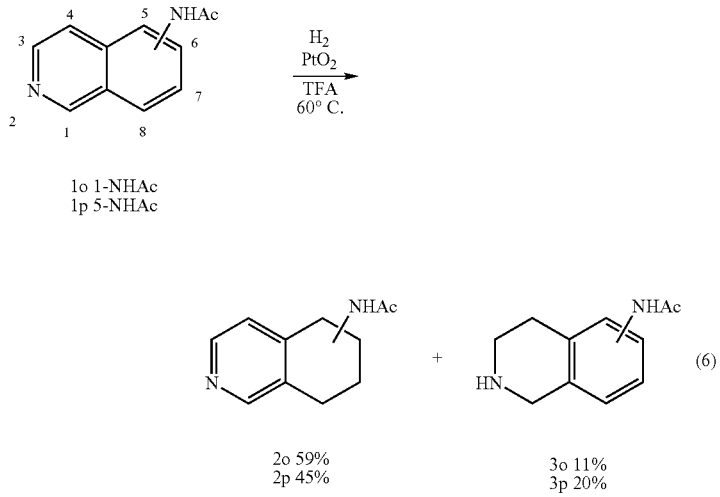

1o 1-NHAc
1p 5-NHAc 2o 59%
2p 45%

3o 11%
3p 20%

Preparation of 5,6,7,8-tetrahydroquinoline-3-carboxylic Acid Methyl Ester

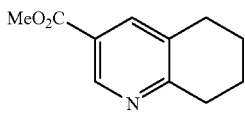

Representative procedure for small scale hydrogenation reactions. To a 2 or 3-neck, 100 ml round bottom flask containing a stir bar was added methyl quinoline-3-carboxylate (170 mg, 0.908 mol) and platinum (IV) oxide (10.3 mg, 5 mol %). The flask was equipped with two outlets sealed with rubber septa and containing Teflon stopcocks. Trifluoroacetic acid (3.0 mL), which was purged with argon gas to remove oxygen, was added via a plastic syringe into the reaction flask under an atmosphere of nitrogen. The stirred reaction mixture was flushed and the flask filled with hydrogen gas via a needle from a balloon through one of the septa-sealed outlets. The Teflon stopcocks were closed and the reaction mixture was warmed to 60° C. and stirred for 5 hours. The progress of the reaction was monitored by GC and TLC. The reaction mixture was cooled to room temperature and aqueous saturated sodium bicarbonate solution was added until the mixture was neutral. The mixture was then extracted with CH$_2$Cl$_2$ (3×30 mL), dried (MgSO$_4$), and the solvent was removed in vacuo. The crude material thus obtained was separated by flash chromatography (silica gel, 10% EtOAc in hexanes). The title compound was obtained as a yellowish liquid (121 mg, 70%) which displayed: $^1$H NMR (CDCl$_3$, 300 MHz): δ 1.80–2.00 (m, 4H), 2.79–2.85 (m, 2H), 2.90–3.00 (m, 2H), 3.91 (s, 3H), 7.95 (s, 1H), 8.93 (s, 1H); $^{13}$C NMR (CDCl$_3$): δ 22.8, 23.1, 28.9, 30.0, 33.1, 52.5, 123.7, 132.5, 138.0, 148.2, 162.6, 166.5; MS m/z: 192 (M+H$^+$). 1,2,3,4-Tetrahydroquinoline-3-carboxylic acid methyl ester also was isolated (19 mg, 11%).

Using the representative procedure for small scale reactions: N-(quinol-2-yl)acetamide (164 mg, 0.881 mmol) provided N-(5,6,7,8-tetrahydroquinolin-2-yl)acetamide (114 mg, 69%); N-(quinol-3-yl)acetamide (138 mg, 0.741 mmol) provided N-(5,6,7,8-tetrahydroquinolin-3-yl)acetamide (89 mg, 63%); N-(quinol-5-yl)acetamide (158 mg, 0.849 mmol) provided N-(5,6,7,8-tetrahydroquinolin-5-yl)acetamide (72 mg, 45%) and N-(1,2,3,4-tetrahydroquinolin-5-yl)acetamide (44 mg, 27%); N-(quinol-6-yl)acetamide (143 mg, 0.768 mmol) provided N-(5,6,7,8-tetrahydroquinolin-6-yl)acetamide (71 mg, 49%) and N-(1,2,3,4-tetrahydroquinolin-6-yl) acetamide (40 mg, 28%), N-(quinol-8-yl)acetamide (186.1 mg, 0.999 mmol) provided N-(5,6,7,8-tetrahydroquinolin-8-yl)acetamide (118.3 mg, 62%)) and N-(1,2,3,4-tetrahydroquinolin-8-yl)acetamide (26.7 mg, 14%), 2-phenylquinoline (162 mg, 0.781 mmol) provided 2-phenyl-5,6,7,8-tetrahydroquinoline (111 mg, 68%) and 2-phenyl-1,2,3,4-tetrahydroquinoline (20 mg, 10%). Reaction of quinoline-2-carboxylic acid methyl ester (160 mg, 0.855 mmol) provided 5,6,7,8-tetrahydroquinoline-2-carboxylic acid methyl ester (83 mg, 51%) and 1,2,3,4-tetrahydroquinoline-2-carboxylic acid methyl ester (33 mg, 20%).

Preparation of N-(2-Methyl-5,6,7,8-tetrahydro-quinolin-4-yl)acetamide

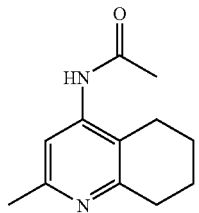

Reaction of N-(2-methyl-quinolin-4-yl)acetamide (136 mg, 0.679 mmol) using the general procedure for small scale hydrogenations (workup with NaOH in place of saturated NaHCO$_3$) provided N-(2-methyl-5,6,7,8-tetrahydroquinolin-4-yl)acetamide (109 mg, 78%): $^1$H NMR δ 1.83–1.90 (m, 4H), 2.21 (s, 3H), 2.47 (s, 3H), 2.46–2.2.53 (m, 2H), 2.84–2.87 (m, 2H), 7.18 (br s, 1H), 7.82 (br s, 1H); $^{13}$C NMR δ 22.7, 22.8, 23.5, 24.6, 25.3, 33.1, 112.3, 117.3, 143.7, 156.4, 157.3, 169.0; MS m/z: 205 (M+H$^+$).

Preparation of N-(5,6,7,8-tetrahydroquinolin-7-yl)acetamide

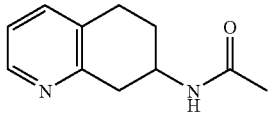

Reaction of N-(quinol-7-yl)acetamide (33 mg, 0.177 mmol) using the general procedure for small scale hydrogenations (workup with NaOH in place of saturated NaHCO3) provided N-(5,6,7,8-tetrahydroquinolin-7-yl)acetamide (8.3 mg, 25%): 1H NMR □ 1.72–1.83 (m, 1H), 1.99 (s, 3H), 2.04–2.20 (m, 2H), 2.72–2.95 (m, 3H), 3.25 (dd, 1H, J=5, 17 Hz), 4.29–4.40 (m, 1H), 5.72 (br s, 1H), 7.05 (dd, 1H, J=4, 8 Hz), 7.38 (d, 1H, J=8 Hz), 8.35 (d, 1H, J=4 Hz); 13C NMR □ 23.9, 26.5, 28.7, 39.0, 45.6, 121.9, 131.4, 137.0, 147.7, 154.8, 170.1; MS m/z: 213 (M+Na+). N-(1,2,3,4-tetrahydroquinolin-7-yl)acetamide also was isolated (6.5 mg, 20%): 1H NMR □ 1.24–1.28 (s, 1H), 1.87–1.95 (m, 2H), 2.70 (dd, 2H, J=6, 6 Hz), 3.28 (dd, 2H, J=5, 5 Hz), 6.46 (d, 1H, J=8 Hz), 6.84 (d, 1H, J=8 Hz), 6.93 (s, 1H), 7.03 (br s, 1H); 13C NMR □ 22.1, 24.7, 26.6, 37.9, 105.6, 108.3, 117.6, 129.6, 136.5, 145.1, 168.1; MS m/z: 213 (M+Na+).

Preparation of N-(2-Methyl-5,6,7,8-tetrahydroquinolin-8-yl)acetamide

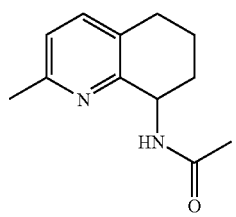

Reaction of N-(2-methyl-quinol-8-yl)acetamide (159 mg, 0.795 mmol) using the general procedure for small scale hydrogenations (workup with NaOH in place of saturated NaHCO$_3$) provided N-(2-methyl-5,6,7,8-tetrahydroquinolin-8-yl)acetamide (92 mg, 57%): $^1$H NMR δ 1.57–1.66 (m, 1H), 1.77–1.86 (m, 2H), 2.02 (s, 3H), 2.44 (s, 3H), 2.43–2.57 (m, 1H), 2.68–2.73 (m, 2H), 4.67–4.74 (m, 1H), 6.79 (br s, 1H), 6.92 (d, 1H, J=8 Hz), 7.24 (d, 1H, J=8 Hz); $^{13}$C NMR δ 21.6, 25.4, 25.8, 29.6, 31.0, 53.0, 123.4, 131.4, 139.2, 155.9, 157.2, 172.2; MS m/z: 227 (M+Na$^+$). N-(2-Methyl-1,2,3,4-tetrahydroquinolin-8-yl)acetamide also was isolated (25 mg, 15%) as a tautomeric mixture of acyclic and cyclized isomers in an approximately 1:2 ratio which exhibited the following data: $^1$H NMR δ 1.21–1.25 (m), 1.45–1.61 (m), 1.90 (s), 1.90–1.95 (m), 2.20 (s), 2.71–2.91 (m), 3.32–3.43 (m), 4.00 (br s), 6.56 (dd, J=8, 8 Hz), 6.63 (dd, J=8, 8 Hz), 6.66 (br s), 6.83 (d, J=8 Hz), 6.87 (d, J=8 Hz), 6.94 (d, J=8 Hz), 7.02 (d, J=8 Hz), 7.06 (br s); MS m/z: 205 (M+H$^+$).

Preparation of 3-methoxy-5,6,7,8-tetrahydroquinoline

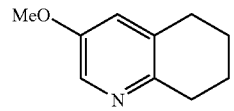

Reaction of 3-methoxyquinoline (181 mg, 1.16 mmol) using the general procedure for small scale hydrogenations provided 3-methoxy-5,6,7,8-tetrahydroquinoline (127 mg, 65%): $^1$H NMR δ 1.74–1.93 (m, 4H), 2.75 (dd, 2H, J=6, 6 Hz), 2.85 (dd, 2H, J=6, 6 Hz), 3.82 (s, 3H), 6.88 (d, 1H, J=3 Hz), 8.06 (d, 1H, J=3 Hz); $^{13}$C NMR δ 23.0, 23.7, 29.4, 32.0, 55.9, 121.5, 132.9, 134.9, 149.8, 154.1; MS m/z: 164.1 (M+H$^+$). A mixture (5 mg) of hydrogenolyzed products (quinoline, 1,2,3,4-tetrahydroquinoline and 5,6,7,8-tetrahydroquinoline as determined by GC analysis by comparison with commercial samples) also was obtained.

Preparation of 5,6,7,8-tetrahydroquinoline-6-carboxylic acid methyl ester

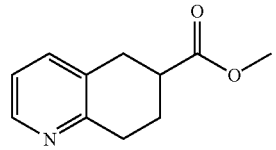

Reaction of quinoline-6-carboxylic acid methyl ester (170 mg, 0.908 mmol) using the general procedure for small scale hydrogenations provided 5,6,7,8-tetrahydroquinoline-6-carboxylic acid methyl ester (49 mg, 30%): $^1$H NMR δ 1.91–2.05 (m, 1H), 2.25–2.34 (m, 1H), 2.74–2.84 (m, 1H), 2.90–3.11 (m, 4H), 3.74 (s, 3H), 7.06 (dd, 1H, J=4, 8 Hz), 7.39 (d, 1H, J=8 Hz), 8.37 (d, 1H, J=4 Hz); $^{13}$C NMR δ 26.1, 31.2, 31.7, 39.6, 52.3, 121.6, 130.5, 137.2, 147.6, 156.3, 175.7; MS m/z: 214 (M+Na$^+$). 1,2,3,4-Tetrahydroquinoline-6-carboxylic acid methyl ester also was isolated (66 mg, 39%).

Preparation of 5,6,7,8-tetrahydroquinoline-8-carboxylic acid methyl ester

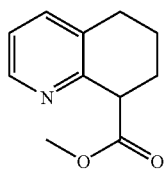

Reaction of quinoline-8-carboxylic acid methyl ester (156 mg, 0.833 mmol) using the general procedure for small scale hydrogenations provided 5,6,7,8-tetrahydroquinoline-8-carboxylic acid methyl ester (58 mg, 36%). 1,2,3,4-Tetrahydroquinoline-8-carboxylic acid methyl ester also was isolated (45 mg, 28%): $^1$H NMR δ 1.87–1.96 (m, 2H), 2.76–2.81 (m, 2H), 3.40–3.45 (m, 2H), 3.83 (s, 3H), 6.43 (dd, 1H, J=7, 8 Hz), 7.03 (d, 1H, J=7 Hz), 7.69 (d, 1H, J=8 Hz), 7.76 (br s, 1H); $^{13}$C NMR δ 21.2, 28.2, 41.6, 51.7, 108.8, 113.9, 122.4, 129.8, 134.1, 148.8, 169.6; MS m/z: 192 (M+H$^+$).

Preparation of N-(5,6,7,8-tetrahydroisoquinolin-1-yl)acetamide

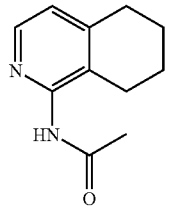

Reaction of N-(isoquinol-1-yl)acetamide (159 mg, 0.854 mmol) using the general procedure for small scale hydrogenations (workup with NaOH in place of saturated NaHCO$_3$) provided N-(5,6,7,8-tetrahydroisoquinolin-1-yl)acetamide (96 mg, 59%): $^1$H NMR δ 1.74–1.76 (m, 4H), 2.16–2.19 (m, 3H), 2.60–2.70 (m, 2H), 2.70–2.76 (m, 2H), 6.86 (d, 1H, J=5 Hz), 8.03 (d, 1H, J=5 Hz); $^{13}$C NMR δ 22.3, 22.8, 23.8, 25.1, 29.6, 122.9, 144.4 (2C), 149.5, 150.2, 170.6; MS m/z: 213 (M+Na$^+$). N-(1,2,3,4-tetrahydroisoquinolin-1-yl)acetamide also was isolated (16 mg, 11%): $^1$H NMR δ 2.28 (m, 3H), 2.96–3.01 (m, 2H), 3.56–3.61 (m, 2H), 7.20 (d, 1H, J=8 Hz), 7.33–7.38 (m, 1H), 7.44–7.49 (m, 1H), 8.27 (d, 1H, J=8 Hz); $^{13}$C NMR δ 27.2, 28.7, 29.7, 39.3, 127.3, 127.5, 128.0, 132.6, 137.9, 162.8, 188.0; MS m/z: 191 (M+H$^+$).

Preparation of N-(5,6,7,8-tetrahydroisoquinolin-5-yl)acetamide

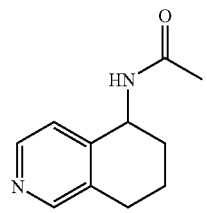

Reaction of N-(isoquinol-5-yl)acetamide (171 mg, 0.918 mmol) using the general procedure for small scale hydrogenations (workup with NaOH in place of saturated NaHCO$_3$) provided N-(5,6,7,8-tetrahydroisoquinolin-5-yl)acetamide (79 mg, 45%): $^1$H NMR δ 1.60–1.70 (m, 1H), 1.70–1.09 (m, 2H), 1.98 (s, 3H), 1.98–2.08 (m, 0.1H), 2.65–2.68 (m, 2H), 5.03–5.11 (m, 1H), 6.63 (br d, 1H), 7.08 (d, 1H, J=5 Hz), 8.17 (s, 1H), 8.20 (d, 1H, J=5 Hz); $^{13}$C NMR δ 20.7, 23.7, 26.4, 30.1, 47.1, 122.9, 133.3, 146.3, 147.5, 150.7, 170.1; MS m/z: 191 (M+H$^+$). N-(1,2,3,4-tetrahydroisoquinolin-5-yl)acetamide also was isolated (35 mg, 20%).

Preparation of (R,S)-8-Amino-5,6,7,8-tetrahydroquinoline by Nitrosation of 5,6,7,8-Tetrahydroquinoline

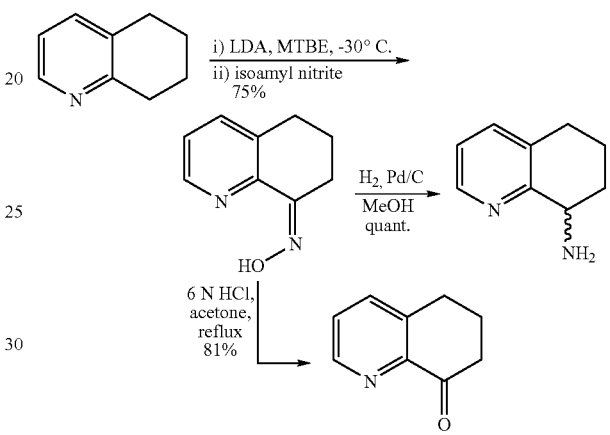

Preparation of 6,7-Dihydro-5H-quinolin-8-one Oxime

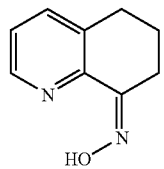

A solution of 5,6,7,8-tetrahydroquinoline (10.83 g, 81.3 mmol) and lithium diisopropylamide (LDA) (22.80 mL, 163 mmol) in dry MTBE (tert-butyl methyl ether) (100 mL was stirred for 10 min while dry N$_2$ (nitrogen) was purged through the system. The solution was then cooled in an acetone-dry ice bath to between –30° C. and –20° C. A 2.5 M solution of "BuLi (n-butyllithium) in hexanes (101.0 mL, 253 mmol) was then added over a period of 5 min. The temperature of the cooling bath was maintained below –20° C. throughout the addition. The thus obtained orange/red mixture was then transferred via cannula to a pre-cooled solution of isoamyl nitrite (38.40 mL, 285 mmol) in dry MTBE (100 mL) at –30° C.; the transfer took about 10 min. The resulting mixture was stirred at –30° C. for 40 min at which time water (4.80 mL) was added in one portion. The quenched mixture was slowly warmed to ambient temperature. A brown solid precipitated from the crude mixture and was collected via filtration. The solid isolate was redissolved in CH$_2$Cl$_2$ (300 mL) and then filtered to remove any insoluble material. The solvent was removed in vacuo and the residue was recrystallized from 1:1 MTBE-hexanes to provide 10.05 g (75%) of the title compound as a beige solid. $^1$H NMR (CDCl$_3$) δ 1.87–1.96 (m, 2H), 2.81 (t, 2H, J=6 Hz), 2.93 (t, 2H, J=8 Hz), 7.18 (dd, 1H, J=9, 6 Hz), 7.48 (dd, 1H, J=9, 1 Hz), 8.52 (dd, 1H, J=6, 1 Hz), 9.63 (br s, 1H); $^{13}$C NMR (CDCl$_3$) δ 20.8, 23.8, 28.9, 123.4, 134.5, 136.7, 148.2, 148.9, 152.7. ES-MS m/z 163 (M+H).

Preparation of 6,7-Dihydro-5H-quinolin-8-one

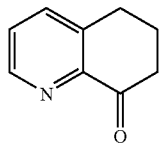

To a stirred solution of 6,7-dihydro-5H-quinolin-8-one oxime (220 mg, 1.36 mmol) in acetone (5.0 mL) was added 6 N HCl (2.0 mL). The resulting mixture was heated to reflux for 16 h, then cooled to room temperature. The reaction mixture was rendered basic with a minimum amount of 3 N NaOH, then extracted with CH$_2$Cl$_2$ (3×30 mL), and the combined organic extracts were dried (MgSO$_4$), filtered and concentrated in vacuo. Flash chromatography of the crude material thus obtained (silica gel, 20:2:1 CH$_2$Cl$_2$—MeOH—NH$_4$OH) afforded 161 mg (81%) of the title compound as a pale yellow solid. $^1$H NMR (CDCl$_3$) δ 2.17–2.25 (m, 2H), 2.82 (t, 2H, J=7 Hz), 3.04 (t, 2H, J=6 Hz), 7.37 (dd, 1H, J=9, 6 Hz), 7.66 (dd, 1H, J=9, 1 Hz), 8.71 (dd, 1H, J=6, 1 Hz); $^{13}$C NMR (CDCl$_3$) δ 22.2, 28.6, 39.2, 126.6, 137.3, 140.5, 147.6, 148.6, 196.5. ES-MS m/z 148 (M+H).

Preparation of (R,S)-8-Amino-5,6,7,8-tetrahydroquinoline

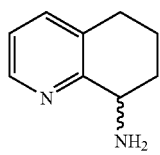

A hydrogenation flask was charged with 6,7-dihydro-5H-quinolin-8-one oxime (266 mg, 1.64 mmol) and MeOH (2.5 mL). The flask was flushed with nitrogen for 5 min, then 10% palladium on carbon (Pd/C) (26 mg) was added in a single portion. The resulting mixture was shaken in a Parr hydrogenator under 45 psi hydrogen for 18 h. The residual material was filtered through a cake of celite eluting with CH$_2$Cl$_2$ (20 mL), and then the solvent was removed in vacuo. This procedure afforded 243 mg (100%) of the title compound as a pale yellow oil. This material displayed spectra identical to those reported above.

Preparation of (R,S)-8-Amino-5,6,7,8-tetrahydroquinoline

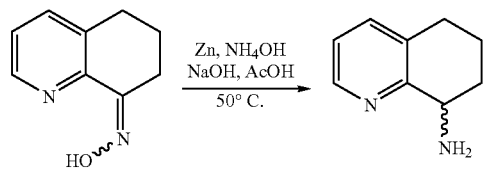

To a mixture of 6,7-dihydro-5H-quinolin-8-one oxime (96 kg, 554 mol) in NH$_4$OH (243 kg), water (279 kg) and 50% NaOH (72 kg), was added acetic acid (40 kg). The line was rinsed with water (18 kg). The mixture was adjusted to 50° C. (ca. 5° C./hr), then zinc dust (144 kg, 2216 mol) was added in 10 portions maintaining a maximum temperature of 65° C. After finishing the addition, the reaction mixture was agitated for 10–16 hours at 50° C., then in-process TLC as performed to confirm the completion of the reaction. The reaction mixture was adjusted to 22° C., then NaCl (108 kg) and toluene (720 kg) were added. After agitating for 1 hr, the mixture was filtered on a Celite pad and rinsed forward with toluene (2 times 90 kg). The layers were separated and the organic layer was set aside. To the aqueous layer, NaCl (45 kg) and toluene (720 kg) were added and the reaction mixture was filtered once more on a Celite pad. After layer separation, the organic layer was set aside. The organic layers were combined and concentrated under vacuum, then dissolved in dichloromethane. The resulting solution was washed with 2.5% NaOH solution (45 kg) and NH$_4$OH (270 kg). The organic layer was set aside, and the aqueous layer was extracted with dichloromethane (297 kg). After phase separation, the organic layers were combined and concentrated to dryness to yield 69 kg (84% yield) of the title compound.

Enzymatic Resolution of (R,S)-8-Amino-5,6,7,8-tetrahydroquinoline

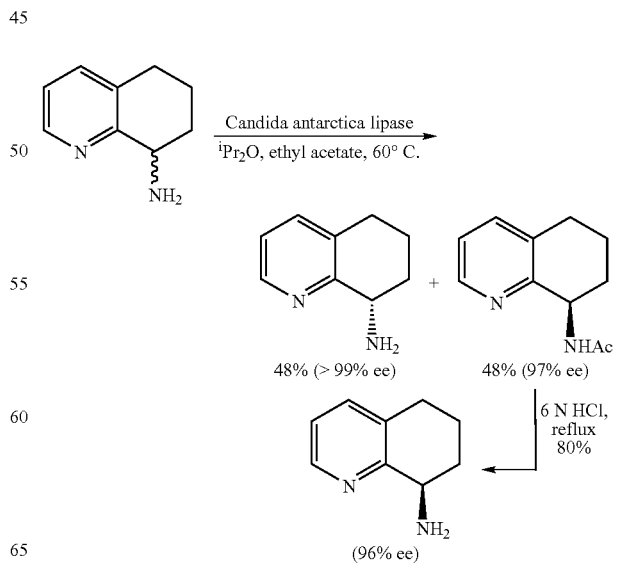

Preparation of (R)-(−)-N-(5,6,7,8-Tetrahydroquinolin-8-yl)-acetamide and (S)-(+)-8-Amino-5,6,7,8-tetrahydroquinoline

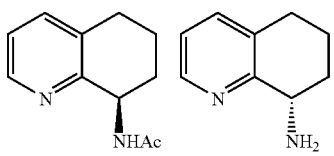

A mixture of (R,S)-8-amino-5,6,7,8-tetrahydroquinoline (1.00 g, 6.75 mmol), *Candida antarctica* lipase (Novozyme 435, 300 mg), and EtOAc (ethyl acetate) (2.64 mL, 27.0 mmol) in dry i-Pr$_2$O (diisopropyl ether) (15 mL) was heated to 60° C. and stirred vigorously for 3 h. At this time, the reaction mixture was filtered through a sintered glass funnel and concentrated. Flash chromatography of the crude material (silica gel, 10:1 CH$_2$Cl$_2$—MeOH then 20:2:1 CH$_2$Cl$_2$—MeOH—NH$_4$OH (ammonium hydroxide)) afforded 0.62 g (R)-(−)-N-(5,6,7,8-tetrahydroquinolin-8-yl)-acetamide (48%) in 97% ee (separated by chiral GC, J&W CycloSil B column, isothermal 150° C., (S)-(+)-enantiomer$_{rt}$=84.25 min, (R)-(−)-enantiomer$_{rt}$=86.16 min). [α]$_D$=−177.5 (c 1.00, CHCl$_3$); $^1$H NMR (CDCl$_3$) δ 1.57–1.63 (m, 1H), 1.74–1.79 (m, 2H), 1.93 (s, 3H), 2.30–2.36 (m, 1H), 2.66–2.71 (m, 2H), 4.78 (dd, 1H, J=14, 6 Hz), 6.97 (dd, 1H, J=8, 5 Hz), 7.13 (br s, 1H), 7.29 (d, 1H, J=8 Hz), 8.19 (d, 1H, J=5 Hz); $^{13}$C NMR (CDCl$_3$) δ 19.5, 23.1, 28.0, 29.3, 49.9, 50.6, 122.1, 132.9, 136.9, 146.4, 154.9, 170.3. ES-MS m/z 191 (M+H). Anal. Calcd. for C$_{11}$H$_{14}$N$_2$O·0.3H$_2$O: C, 67.53; H, 7.52; N, 14.32. Found: C, 67.60; H, 7.20; N, 14.12.

Also isolated was 0.48 g (48%) (S)-(+)-8-amino-5,6,7,8-tetrahydroquinoline in >99% ee (separated by chiral GC, J&W CycloSil B column, initial temperature: 160° C., initial time: 0 min rate: 1° C./min, final temperature: 130° C., final time: 0 min, (S)-(+)-enantiomer$_{rt}$=12.43 min, (R)-(−)-enantiomer$_{rt}$=13.13 min). [α]$_D$=+124.1 (c 0.99, CHCl$_3$); $^1$H NMR (CDCl$_3$) δ 1.52–1.62 (m, 2H), 1.78–1.85 (m, 1H), 1.91 (br s, 2H), 2.02–2.06 (m, 1H), 2.60–2.65 (m, 2H), 3.83–3.87 (m, 2H), 6.91 (dd, 1H, J=8, 5 Hz), 7.21 (dd, 1H, J=8, 1 Hz), 8.26 (d, 1H, J=5 Hz); $^{13}$C NMR (CDCl$_3$) δ 19.6, 28.7, 31.7, 51.0, 121.3, 131.2, 136.4, 146.7, 159.2. ES-MS m/z 149 (M+H).

Preparation of (R)-(−)-8-Amino-5,6,7,8-tetrahydroquinoline

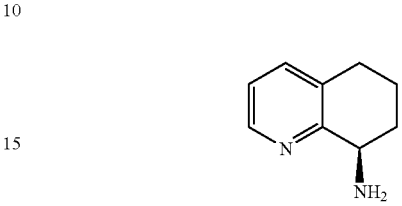

A stirred solution of (R)-(−)-N-(5,6,7,8-tetrahydroquinolin-8-yl)-acetamide (230 mg, 1.21 mmol, 97% ee) in 6 N aqueous HCl (4.0 mL) was heated to 130° C. for 2 h. At this time, the reaction mixture was cooled to room temperature and cautiously rendered basic with a minimum amount of saturated aqueous NaOH, then diluted with CH$_2$Cl$_2$ (10 mL). The phases were separated and the aqueous phase was washed with CH$_2$Cl$_2$ (5×20 mL), then the combined organic phases were dried (MgSO$_4$) and concentrated. Flash chromatography through a plug of silica gel (elution with 20:2:1 CH$_2$Cl$_2$—MeOH—NH$_4$OH) afforded 143 mg (80%) of (R)-(−)-8-amino-5,6,7,8-tetrahydroquinoline in 96% ee (separated by chiral GC, J&W CycloSil B column, initial temperature: 160° C., initial time: 0 min, rate: 1° C./min, final temperature: 130° C., final time: 0 min, (S)-(+)-enantiomer$_{rt}$=12.43 min, (R)-(−)-enantiomer$_{rt}$=13.13 min). [α]$_D$=−125.7 (c 0.56, CHCl$_3$); $^1$H NMR (CDCl$_3$) δ 1.52–1.62 (m, 2H), 1.78–1.85 (m, 1H), 1.91 (br s, 2H), 2.02–2.06 (m, 1H), 2.60–2.65 (m, 2H), 3.83–3.87 (m, 2H), 6.91 (dd, 1H, J=8, 5 Hz), 7.21 (dd, 1H, J=8, 1 Hz), 8.26 (d, 1H, J=5 Hz); $^{13}$C NMR (CDCl$_3$) δ 19.6, 28.7, 31.7, 51.0, 121.3, 131.2, 136.4, 146.7, 159.2. ES-MS m/z 149 (M+H).

Further examples of enzymatic resolution are provided in the table below.

TABLE 2

Enzymatic resolution of amines using *Candida antarctica* lipase

| substrate | conditions[a] | conversion[b] (%) | ee[c] (%) (S)-1 | ee[c] (%) (R)-2 | isolated yield (%) (S)-1 | isolated yield (%) (R)-2 |
|---|---|---|---|---|---|---|
| (tetrahydroquinolin-8-yl-amine structure) | A | 50 | >99 | 98 | 48 | 48 |

TABLE 2-continued
Enzymatic resolution of amines using *Candida antarctica* lipase
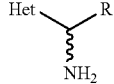
| substrate | conditions[a] | conversion[b] (%) | ee[c] (%) | | isolated yield (%) | |
|---|---|---|---|---|---|---|
| | | | (S)-1 | (R)-2 | (S)-1 | (R)-2 |
| 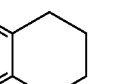 | A | 50 | >99 | 98 | 48 | 48 |
| 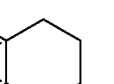 | A | 51 | 99 | 94 | 43 | 51 |
| 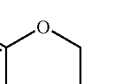 | B | 50 | 99 | 98 | 45 | 47 |
| 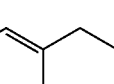 | B | 50 | 99 | 98 | 43 | 47 |
|  | A | 51 | 91 | 88 | 38 | 48 |
| 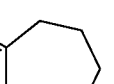 | B | 55 | 99 | 79 | 42 | 55 |
| 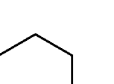 | A | 58 | 61 | 45 | 41 | 55 |
|  | A | 55 | 94 | 79 | 39 | 53 |

TABLE 2-continued

Enzymatic resolution of amines using *Candida antarctica* lipase

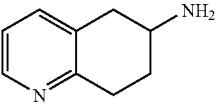

| substrate | conditions[a] | conversion[b] (%) | ee[c] (%) | | isolated yield (%) | |
|---|---|---|---|---|---|---|
| | | | (S)-1 | (R)-2 | (S)-1 | (R)-2 |
| (tetrahydroquinolin-5-ylamine structure) | A | 56 | 43 | 46 | N/d | N/d |

[a]All reactions were performed at 60° C. Reaction times varied from 2 h to 24 h. Condition A: reaction carried out in isopropyl ether with 4–5 equiv EtOAc; Condition B: reaction carried out in neat EtOAc.
[b]Percent conversion determined by $^1$HNMR..
[c]Enantiomeric excess determined by chiral GC.

General Procedure for Resolution Reaction

A mixture of the amine (1 equiv; ~0.2 M), *Candida antarctica* lipase B (Novozyme 435) (30 wt %) and ethyl acetate (4–5 equiv) in dry isopropyl ether (Condition A) or neat ethyl acetate (Condition B) were heated to 60° C. and stirred vigorously. Anhydrous solvents (99.9%) purchased from Aldrich were used. The progress of the reaction was monitored by GC using a chiral J&W CycloSil B column. Upon completion of the reaction (typically 2–24 hours) the mixture was filtered through a glass sintered funnel, was washed with EtOAc or methanol and concentrated in vacuo. The unreacted amine and the acetamide were separated by chromatography on silica gel. The enantiomeric excess of the amine and the acetamide were determined by chiral GC by comparison of the retention times with independently prepared racemic samples. Optical rotations were measured using a P3001 Kruss polarimeter.

Preparation of (R)—N-(5,6,7,8-tetrahydroquinolin-5-yl)acetamide and (S)-5,6,7,8-tetrahydroquinolin-5-ylamine

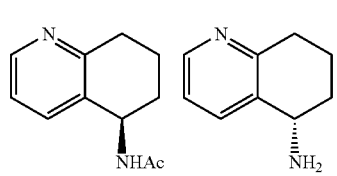

Following the general procedure, 5,6,7,8-tetrahydroquinolin-5-ylamine (213.2 mg, 1.44 mmol), CALB (64 mg), EtOAc (0.56 mL) and iPr$_2$O (4.8 mL) were stirred for 6 hours. The conversion determined from $^1$H NMR by integration of the peaks at 5.07 ppm (C$\underline{H}$NHAc) and 3.91 ppm (C$\underline{H}$NH$_2$) was 50%. Flash chromatography of the material on silica gel using 1:10 MeOH:CH$_2$Cl$_2$ then 20:2:1 CH$_2$Cl$_2$—MeOH—NH$_4$OH furnished (R)—N-(5,6,7,8-tetrahydroquinolin-5-yl)acetamide ((132 mg, 48%) in 98% ee (chiral GC method: isothermal at 85° C. for 220 minutes ramp 5° C./min to 210° C., hold 5 min, (S)-enantiomer$_{rt}$=248.2 min, (R)-enantiomer$_{rt}$=248.5 min); $[\alpha]_D$=+110° (c 1.32, CHCl$_3$); $^1$H NMR (CDCl$_3$, 300 MHz) δ 1.69–1.81 (m, 1H), 1.84–2.00 (m, 2H), 2.04 (s, 3H), 2.01–2.18 (m, 1H), 2.86–2.99 (m, 2H), 5.19–5.27 (m, 1H), 5.78 (br s, 1H), 7.10 (dd, 11H, J=7.8, 4.8 Hz), 7.58 (d, 1H, J=7.8 Hz), 8.41 (d, 1H, J=4.8 Hz); $^{13}$C NMR (CDCl$_3$) δ 20.2, 23.8, 30.1, 32.6, 47.4, 121.9, 133.0, 136.9, 148.7, 157.7, 170.0; MS m/z: 191 (M+H$^+$). The unreacted (S)-5,6,7,8-tetrahydroquinolin-5-ylamine (was isolated in 48% yield (103 mg) and 99% ee (chiral GC: (S)-enantiomer$_{rt}$=236.0 min, (R)-enantiomer$_{rt}$=236.6 min); $[\alpha]_D$=+39° (c 1.03, CHCl$_3$); $^1$H NMR (CDCl$_3$, 300 MHz) δ 1.50–1.70 (m, 3H), 1.74–1.85 (m 1H), 1.86–2.09 (m, 2H), 2.76–2.99 (m, 2H), 3.94 (m, 1H), 7.07 (dd, 1H, J=7.8, 4.5 Hz), 7.70 (d, 1H, J=7.8 Hz), 8.35 (dd, 1H, J=4.5, 1.5 Hz); $^{13}$C NMR (CDCl$_3$) δ 19.8, 32.9, 34.0, 49.6, 121.7, 136.2, 136.6, 148.1, 157.3; MS m/z: 149 (M+H$^+$).

Preparation of (R)—N-(5,6,7,8-tetrahydroisoquinolin-5-yl)acetamide and (S)-5,6,7,8-tetrahydroisoguinolin-5-ylamine

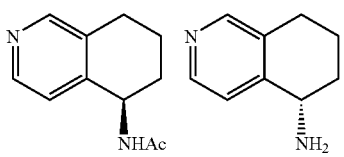

Following the general procedure, 5,6,7,8-tetrahydroisoquinolin-5-ylamine (268.3 mg, 1.81 mmol), CALB (80 mg), EtOAc (0.71 mL) and iPr$_2$O (6.0 mL) were stirred for 23 hours. The conversion determined from $^1$H NMR by integration of the peaks at 5.16 ppm (C$\underline{H}$NHAc) and 3.90 ppm (C$\underline{H}$NH$_2$) was 51%. Flash chromatography of the material on silica gel using 1:4 MeOH:CH$_2$Cl$_2$ then 4:1:1 CH$_2$Cl$_2$—MeOH—NH$_4$OH furnished the (R)—N-(5,6,7,8-tetrahydroquinolin-5-yl)acetamide ((181 mg, 51%) in 94% ee (chiral GC method: 160° C. for 20 min, ramp rate 5° C./min to 200° C., hold at 200° C. for 20 min, (S)-enantiomer$_{rt}$=38.3 min, (R)-enantiomer$_{rt}$=39.1 min); $[\alpha]_D$=+95° (c 1.81, CHCl$_3$); $^1$H NMR (CDCl$_3$, 300 MHz) δ 1.58–1.69 (m, 1H), 1.70–1.92

(m, 2H), 1.96 (s, 3H), 1.94 (2.04 (m, 1H), 2.61–2.68 (m, 2H), 5.00–5.10 (m, 1H), 6.82 (br d, 1H, J=8.7 Hz), 7.05 (d, 1H, J=5.4 Hz), 8.13 (s, 1H), 8.17 (d, 1H, J=5.4 Hz); $^{13}$C NMR (CDCl$_3$) δ 18.6, 21.6, 24.4, 28.1, 45.1, 120.9, 131.4, 144.6, 145.4, 148.6, 168.4; MS m/z: 191 (M+H$^+$), 132 (M–NHAc). The unreacted (S)-5,6,7,8-tetrahydroisoquinolin-5-ylamine (was isolated in 43% yield (114 mg) and 99% ee (chiral GC: (S)-enantiomer$_{rt}$=15.9 min, (R)-enantiomer$_{rt}$=16.2 min); [α]$_D$+63° (c 1.14, CHCl$_3$). $^1$H NMR (CDCl$_3$, 300 MHz) δ 1.26–1.69 (m, 3H), 1.70–1.85 (m, 1H), 1.86–2.11 (m, 2H), 2.67–2.79 (m, 2H), 3.91 (t, 1H, J=5.4 Hz), 7.32 (d, 1H, J=4.3 Hz), 8.32 (s, 1H), 8.37 (d, 1H, J=4.3 Hz); $^{13}$C NMR (CDCl$_3$) δ 20.1, 26.7, 33.7, 49.3, 122.5, 132.6, 147.6, 149.9, 150.8; MS m/z: 149 (M+H$^+$), 132 (M–NH$_2$).

Preparation of (R)—N-(5,6,7,8-tetrahydroquinoxalin-5-yl)acetamide and (S)-5,6,7,8-tetrahydroquinoxalin-5-ylamine

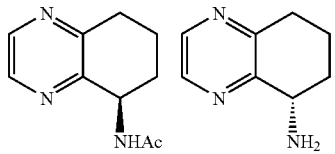

Following the general procedure, 5,6,7,8-tetrahydroquinoxalin-5-ylamine (263 mg, 1.76 mmol), CALB (45 mg) and EtOAc (7.0 mL) were stirred for 2 hours. The conversion determined from $^1$H NMR by integration of the peaks at 4.94 ppm (CHNHAc) and 4.01 ppm (CHNH$_2$) was 50%. Flash chromatography of the material on silica gel using 1:4 MeOH:EtOAc followed by 1:1:4 NH$_4$OH:MeOH:EtOAc furnished the (R)—N-(5,6,7,8-tetrahydroquinoxalin-5-yl)acetamide ((157 mg, 47%) in 98% ee (chiral GC method: 130° C. for 180 min, (S)-enantiomer$_{rt}$=183.5 min, (R)-enantiomer$_{rt}$=183.7 min); [α]$_D$=−78° (c 1.40, CHCl$_3$); $^1$H NMR (CDCl$_3$, 300 MHz) δ 1.62–1.75 (m, 1H), 1.85–2.04 (m, 2H), 2.06 (s, 3H), 2.48–2.57 (m, 1H), 2.90–3.13 (m, 2H), 4.96–5.03 (m, 1H), 6.34 (br s, 1H), 8.35 (d, 1H, J=2.4 Hz), 8.39 (d, 1H, J=2.4 Hz); $^{13}$C NMR (CDCl$_3$) δ 19.9, 23.6, 29.7, 31.8, 50.6, 142.1, 143.3, 152.0, 154.0, 170.7; MS m/z: 214 (M+Na$^+$). The unreacted (S)-5,6,7,8-tetrahydroquinoxalin-5-ylamine (was isolated in 45% yield (118 mg) and 99% ee ((S)-enantiomer$_{rt}$=25.9 min, (R)-enantiomer$_{rt}$=29.0 min); [α]$_D$=+61° (c 0.71, CHCl$_3$); $^1$H NMR (CDCl$_3$, 300 MHz): δ 1.62–1.79 (m, 1H), 1.80–2.18 (m, 4H), 2.18–2.30 (m, 1H), 2.91–3.01 (m, 2H), 4.07 (dd, 1H, J=8.4, 5.4 Hz), 8.32–8.38 (m, 2H); $^{13}$C NMR (CDCl$_3$): δ 19.7, 31.7, 32.2, 51.5, 142.0, 142.5, 152.6, 155.4; MS m/z: 150 (M+H$^+$), 133 (M–NH$_2$).

Preparation of (R)—N-(3,4-dihydro-2H-pyrano[3,2-b]pyridin-4-yl)acetamide and (S)-3,4-dihydro-2H-pyrano[3,2-b]pyridin-4-ylamine

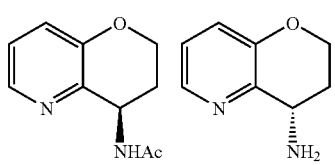

Following the general procedure, 3,4-dihydro-2H-pyrano[3,2-b]pyridin-4-ylamine (243 mg, 1.62 mmol), CALB (73 mg) and EtOAc (6.0 mL) were stirred for 2 hours. The conversion determined from $^1$H NMR by integration of the peaks at 7.93 ppm and 8.16 ppm was 50% (CHNH$_2$ and CHNHAc signals were not distinct). Flash chromatography of the material on silica gel using 1:10 MeOH:CH$_2$Cl$_2$ followed by 1:1:10 NH$_4$OH:MeOH:CH$_2$Cl$_2$ furnished the (R)—N-(3,4-dihydro-2H-pyrano[3,2-b]pyridin-4-yl)acetamide ((145 mg, 47%) in 98% ee (chiral GC method: 140° C. for 16 min, ramp rate 5° C./min to 160° C., hold at 160° C. for 50 min, (S)-enantiomer$_{rt}$=41.5 min, (R)-enantiomer$_{rt}$=40.9 min); [α]$_D$=−69° (c 1.45, CHCl$_3$); $^1$H NMR (CDCl$_3$, 300 MHz) δ 1.91–2.00 (m, 1H), 1.97 (s, 3H), 2.47–2.57 (m, 1H), 4.18–4.22 (m, 2H), 4.85–4.92 (m, 1H), 6.97 (m, 2H), 7.24 (br s, 1H), 7.93–7.95 (dd, 1H, J=1.8, 3.9 Hz); $^{13}$C NMR (CDCl$_3$) δ 23.3, 28.9, 47.2, 64.4, 124.3, 124.7, 141.3, 141.7, 152.0, 170.9; MS m/z: 215 (M+Na$^+$). The unreacted (S)-3,4-dihydro-2H-pyrano[3,2-b]pyridin-4-ylamine (was isolated in 43% yield (104 mg) and 99% ee ((S)-enantiomer$_{rt}$=14.7 min, (R)-enantiomer$_{rt}$=15.6 min); [α]$_D$=−13° (c 0.72, CHCl$_3$); $^1$H NMR (CDCl$_3$, 300 MHz): δ 1.84 (br s, 2H), 1.90–2.01 (m, 1H), 2.24–2.34 (m, 1H), 4.12 (dd, 1H, J=5.7, 6.9 Hz), 4.18–4.26 (m, 1H), 4.28–4.36 (m, 1H), 7.06–7.13 (m, 2H), 8.15 (dd, 1H, J=1.8, 3.6 Hz); $^{13}$C NMR (CDCl$_3$) δ 31.5, 47.8, 64.2, 123.8, 124.5, 142.1, 147.0, 151.1; MS m/z: 151.0 (M+H$^+$), 134.0 (M–NH$_2$); Anal. Calc. for C$_8$H$_{10}$N$_2$O.0.1H$_2$O: C, 63.22; H, 6.76; N, 18.43. Found: C, 62.99; H, 6.81; N, 18.22.

Preparation of (R)—N-(2-methyl-5,6,7,8-tetrahydroquinolin-8-yl)acetamide and (S)-2-methyl-5,6,7,8-tetrahydroquinolin-8-ylamine

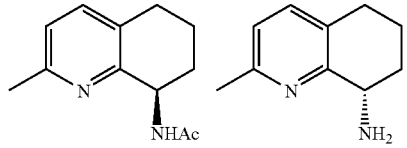

Following the general procedure, 2-methyl-5,6,7,8-tetrahydroquinolin-8-ylamine (412.7 mg, 2.78 mmol), CALB (128 mg), EtOAc (0.63 mL) and iPr$_2$O (7 mL) were stirred for 9 hours. The conversion determined from $^1$H NMR by integration of the peaks at 4.73 ppm (CHNHAc) and 4.00 ppm (CHNH$_2$) was 51%. Flash chromatography of the material on silica gel using 1:10 MeOH:CH$_2$Cl$_2$ then 10:1:1 CH$_2$Cl$_2$—MeOH—NH$_4$OH furnished (R)-N-(2-methyl-5,6,7,8-tetrahydroquinolin-8-yl)acetamide ((167 mg, 47%) in 88% ee (chiral GC method: initial temperature 140° C., initial time 22 minutes, ramp rate 1° C./min, final temperature 150° C., final time 70 min, (S)-enantiomer$_{rt}$=89.4 min, (R)-enantiomer$_{rt}$=91.6 min); [α]$_D$=−102° (c 1.67, CHCl$_3$); $^1$H NMR (CDCl$_3$, 300 MHz) δ 1.56–1.66 (m, 1H), 1.82–1.91 (m, 2H), 2.08 (s, 3H), 2.51 (s, 3H), 2.61 (ddd, 1H, J=13.2, 5.1, 5.1 Hz), 2.76 (t, 1H, J=6.6 Hz), 4.72–4.79 (m, 1H), 6.61 (br s, 1H), 6.98 (d, 1H, J=7.8 Hz), 7.31 (d, 1H, J=7.8 Hz); $^{13}$C NMR (CDCl$_3$) δ 20.1, 23.8, 24.2, 28.2, 29.6, 51.5, 122.4, 130.1, 137.8, 154.4, 155.7, 170.8; MS m/z: 205 (M+H$^+$), 146 (M–NHAc). The unreacted (S)-2-methyl-5,6,7,8-tetrahydroquinolin-8-ylamine (was isolated in 38% yield (107 mg) and 91% ee (chiral GC: (S)-enantiomer$_{rt}$=19.9 min, (R)-enantiomer$_{rt}$=20.6 min); [α]$_D$=+65° (c 1.07, CHCl$_3$); $^1$H NMR (CDCl$_3$, 300 MHz) δ 1.62–1.82 (m, 2H), 1.84–2.00 (m, 3H), 2.11–2.20 (m, 1H), 2.49 (s, 3H), 2.61–2.82 (m, 2H), 3.93–4.00 (m, 1H), 6.91 (d, 1H), J=7.8

Hz), 7.25 (d, 1H, J=7.8 Hz); $^{13}$C NMR (CDCl$_3$) δ 20.4, 24.6, 29.1, 32.6, 51.8, 121.7, 128.6, 137.6, 155.9, 159.0; MS m/z: 163 (M+H$^+$).

Preparation of (R)—N-(6,7-dihydro-5H[1]pyrindin-7-yl)acetamide and (S)-6,7-dihydro-5H-[1]pyrindin-7-ylamine

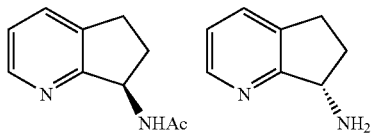

Following the general procedure, 6,7-dihydro-5H-[1]pyrindin-7-ylamine (271 mg, 2.02 mmol), CALB (81 mg) and EtOAc (6.5 mL) were stirred for 7 hours. The conversion determined from $^1$H NMR by integration of the peaks at 5.17 ppm (CHNHAc) and 4.21 ppm (CHNH$_2$) was 55%. Flash chromatography of the material on silica gel using 1:10 MeOH:CH$_2$Cl$_2$ followed by 1:1:4 NH$_4$OH:MeOH:CH$_2$Cl$_2$ furnished (R)—N-(6,7-dihydro-5H-[1]pyrindin-7-yl)acetamide ((194 mg, 41%). The two enantiomers of the acetamide could not be resolved by GC nor HPLC, and hence the % ee had to be determined indirectly. A small sample of the acetamide was treated with 1N HCl to convert it to the amine, and the resulting amine was resolved by chiral GC (chiral GC method: 85° C. for 120 min, ramp rate 5° C./min to 210° C., final time 5 min; (S)-enantiomer$_{rt}$=124.3 min, (R)-enantiomer$_{rt}$=126.1 min) to give % ee of 79%; [α]$_D$=−41° (c 1.49, CHCl$_3$); $^1$H NMR (CDCl$_3$, 300 MHz) δ 1.75–1.89 (m, 1H), 2.07 (s, 3H), 2.80–2.98 (m, 3H), 5.19–5.27 (m, 1H), 6.32 (br s, 1H), 7.14 (dd, 1H, J=7.5, 5.0 Hz), 7.55 (d, 1H), J=7.5 Hz), 8.39 (d, 1H, J=4.5 Hz); $^{13}$C NMR (CDCl$_3$) δ 23.6, 28.3, 33.9, 55.7, 123.0, 133.3, 137.2, 148.2, 148.4, 162.7, 171.0. The unreacted (S)-6,7-dihydro-5H[1]pyrindin-7-ylamine (was isolated in 42% yield (113 mg) and 99% ee (chiral GC, (S)-enantiomer$_{rt}$=124.3 min, (R)-enantiomer$_{rt}$=126.1 min) and displayed spectra identical to the starting material: $^1$H NMR (CDCl$_3$, 300 MHz) δ 1.68–1.88 (m, 1H), 2.50–2.61 (m, 3H), 2.75–2.86 (m, 1H), 2.92 (ddd, 1H, J=13.2, 9.0, 3.0 Hz), 4.32 (dd, 1H, J=7.8, 7.8 Hz), 7.08 (dd, 1H, J=7.8, 4.8 Hz), 7.51 (d, 1H, J=7.8 Hz), 8.40 (d, 1H, J=4.8 Hz). The dark color of the amine after purification by column chromatography prevented determination of its optical rotation.

Preparation of (R)—N-(6,7,8,9-tetrahydro-5H-cyclohepta[b]pyridin-9-yl)acetamide and (S)-6,7,8,9-tetrahydro-5H-cyclohepta[b]pyridin-9-ylamine

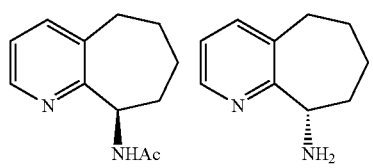

Following the general procedure, 6,7,8,9-tetrahydro-5H-cyclohepta[b]pyridin-9-ylamine (195 mg, 1.20 mmol), CALB (59 mg), EtOAc (0.48 mL) and iPr$_2$O (4.6 mL) were stirred for 24 hours. The conversion determined from $^1$H NMR by integration of the peaks at 5.05 ppm (CHNHAc) and 4.34 ppm (CHNH$_2$) was 58%. Flash chromatography of the material on silica gel using 1:10 MeOH:CH$_2$Cl$_2$ followed by 1:1:4 NH$_4$OH:MeOH:CH$_2$Cl$_2$ furnished the (R)—N-(6,7,8,9-tetrahydro-5H-cyclohepta[b]pyridin-9-yl)acetamide ((134 mg, 55%) in 45% ee (chiral GC method: 180° C. for 15 min, ramp rate of 10° C./min to 210° C., hold 10 min, (S)-(−)-enantiomer$_{rt}$=17.4 min, (R)-(+)-enantiomer$_{rt}$=17.1 min); [α]$_D$=−10° (c 1.34, CHCl$_3$); $^1$H NMR (CDCl$_3$, 300 MHz)δ 1.09–1.31 (m, 2H), 1.80–2.03 (m, 3H), 2.06 (s, 3H), 2.24 (d, 1H, J=13.5 Hz), 2.65–2.71 (m, 1H), 2.75–2.85 (m, 1H), 4.96–5.01 (m, 1H), 7.06 (dd, 1H, J=7.0, 4.8 Hz), 7.38 (d, 1H, J=7.0 Hz), 8.11 (br s, 1H), 8.28 (d, 1H, J=4.8 Hz); $^{13}$C NMR (CDCl$_3$) δ 24.0, 27.3, 30.1, 34.5, 34.8, 53.8, 122.8, 137.0, 137.5, 145.5, 159.2, 169.6; MS m/z: 205 (M+H$^+$). The unreacted (S)-6,7,8,9-tetrahydro-5H-cyclohepta[b]pyridin-9-ylamine (was isolated in 41% yield (81 mg) and 61% ee (chiral GC, (S)-enantiomer$_{rt}$=5.81 min, (R)-enantiomer$_{rt}$=6.00 min)[α]$_D$=+2° (c 1.13, CHCl$_3$); and displayed spectra identical to the starting material: $^1$H NMR (CDCl$_3$, 300 MHz) δ 1.20–1.35 (m, 1H), 1.36–1.53 (m, 1H), 1.75–2.01 (m, 4H), 2.15 (br s, 2H), 2.69–2.77 (m, 2H), 4.16 (d, 1H, J=8.7 Hz), 6.95–7.06 (m, 1H), 7.32 (d, 1H, J=6.0 Hz), 8.34 (br s, 1H), Preparation of (R)—N-(4,5,6,7-tetrahydrobenzofuran-7-yl)acetamide and (S)-4,5,6,7-tetrahydrobenzofuran-7-ylamine

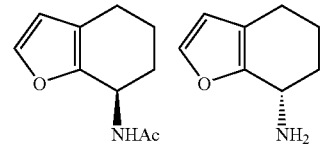

Following the general procedure, 4,5,6,7-tetrahydrobenzofuran-7-ylamine (150 mg, 1.09 mmol), CALB (45 mg), EtOAc (0.43 mL) and iPr$_2$O (4.0 mL) were stirred for 17 hours. The conversion determined from $^1$H NMR by integration of the peaks at 5.09 ppm (CHNHAc) and 3.95 ppm (CHNH$_2$) was 55%. Flash chromatography of the material on silica gel using 1:20 MeOH:CH$_2$Cl$_2$ followed by 1:1:4 NH$_4$OH:MeOH:CH$_2$Cl$_2$ furnished (R)—N-(4,5,6,7-tetrahydrobenzofuran-7-yl)acetamide ((104 mg, 53%) in 79% ee (chiral GC method: 120° C. for 15 min, ramp rate of 2° C./min to 160° C., hold 20 min at 160° C., (S)-(−)-enantiomer$_{rt}$43.6 min (R)-(+)-enantiomer$_{rt}$=45.8 min); [α]$_D$=+58° (c 1.04, CHCl$_3$); $^1$H NMR (CDCl$_3$, 300 MHz) δ 1.65–1.86 (m, 3H), 1.90–1.2.04 (m, 1H), 1.94 (s, 3H), 2.30–2.50 (m, 2H), 5.09 (br s, 1H), 6.16 (s, 1H), 7.24 (s, 1H); $^{13}$C NMR (CDCl$_3$) δ 20.6, 22.4, 23.6, 31.0, 43.6, 110.7, 120.9, 142.2, 148.8, 170.1; MS m/z: 180 (M+H$^+$). The unreacted (S)-4,5,6,7-tetrahydrobenzofuran-7-ylamine (was isolated in 39% yield (59 mg) and 94% ee (chiral GC, (S)-enantiomer$_{rt}$=12.6 min, (R)-enantiomer$_{rt}$=13.5 min); [α]$_D$=−18° (c 0.59, CHCl$_3$); $^1$H NMR (CDCl$_3$, 300 MHz): δ 1.50–1.75 (m, 4H), 1.76–1.90 (m, 1H), 2.01–2.20 (m, 1H), 2.30–2.50 (m, 2H), 3.94 (t, 1H, J=5.7 Hz), 6.17 (d, 1H, J=1.5 Hz), 7.26 (d, 1H, J=1.5 Hz); $^{13}$C NMR (CDCl$_3$): δ 21.1, 22.6, 34.0, 45.5, 110.5, 117.9, 141.3, 153.6; MS m/z: 160 (M+Na$^+$).

Preparation of (R)—N-(5,6,7,8-tetrahydroquinolin-6-yl)acetamide and (S)-5,6,7,8-tetrahydroquinolin-6-ylamine

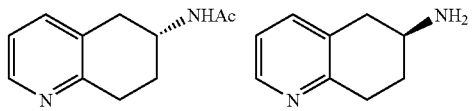

Following the general procedure, 5,6,7,8-tetrahydroquinolin-6-ylamine (251.4 mg, 1.70 mmol), CALB (75 mg), EtOAc (0.60 mL) and iPr$_2$O (4.8 mL) were stirred for 23 hours. The enantiomeric excess of 5,6,7,8-tetrahydroquinolin-6-ylamine and N-(5,6,7,8-tetrahydroquinolin-6-yl)acetamide in a reaction mixture at this point was 15% and 62% respectively (chiral GC method: 160° C. for 10 minutes, ramp 1° C./min to 150° C., hold 50 min: (S)-2j$_{rt}$=81.7 min, (R)-2j$_{rt}$=82.2 min); (S)-1j$_{rt}$=10.2 min, (R)-1j$_{rt}$=10.5 min). Further 2.0 ml of EtOAc and 75 mg of CAL were added, and the reaction mixture was stirred for 5 hours. The enantiomeric excess of (S)-5,6,7,8-tetrahydroquinolin-6-ylamine and (R)—N-(5,6,7,8-tetrahydroquinolin-6-yl)acetamide in the crude reaction mixture was 43% and 46% respectively, and the reaction was stopped.

Racemization of (R)—N-(5,6,7,8-Tetrahydroquinolin-8-yl)-acetamide and (R)-(5,6,7,8-tetrahydroquinolin-8-yl)-amine

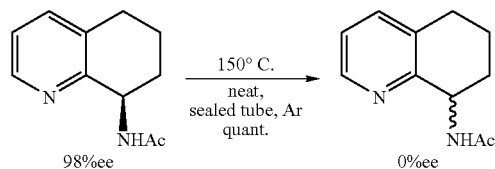

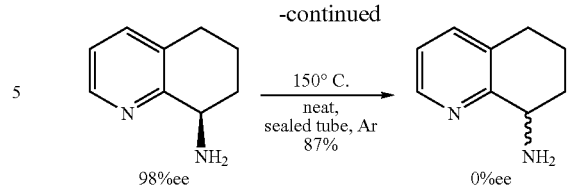

(R)-5,6,7,8-N-(Tetrahydroisoquinolin-8-yl)acetamide (200 mg; 98% ee determined by chiral GC) was placed in a sealed pressure tube flushed with argon. The reaction tube was placed in a hot (150° C.) oil bath until the starting material melted and heating was continued for 40 minutes. The material at this point had the enantiomeric excess of 0% ee and its $^1$H NMR was unchanged in comparison with the ee % of the starting material. The yield of the racemized product was 200 mg (100%).

(R)-(5,6,7,8-tetrahydroquinolin-8-yl)-amine (38 g; 98% ee determined by chiral GC) was heated to 150° C. in a round bottom flask using a heating mantle. Complete racemization was observed (chiral GC) after 30 minutes and the material turned dark in color. The reaction vessel was cooled to room temperature. Kugelrohr distillation of the material provided the amine in 87% yield (33 g).

Racemization of (R)-5,6,7,8-N-(Tetrahydroisoguinolin-5-yl)acetamide (R)-5,6,7,8-N-(Tetrahydroisoquinolin-5-yl)acetamide (60 mg; 94% ee determined by chiral GC) was placed in a sealed pressure tube flushed with argon. The reaction tube was placed in a hot (150° C.) oil bath until the starting material melted and heating was continued for 2 hours. The material at this point had the enantiomeric excess of 0% ee and its $^1$H NMR was unchanged in comparison with the ee % of the starting material. The yield of the racemized product was 60 mg (100%).

Asymmetric Synthesis of (R)-(−)-8-Amino-5,6,7,8-tetrahydroquinoline

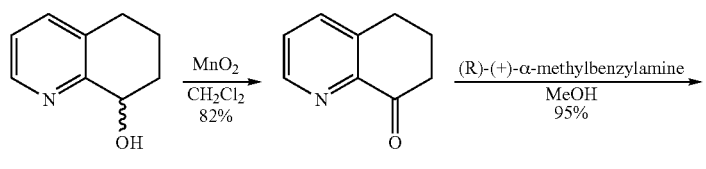

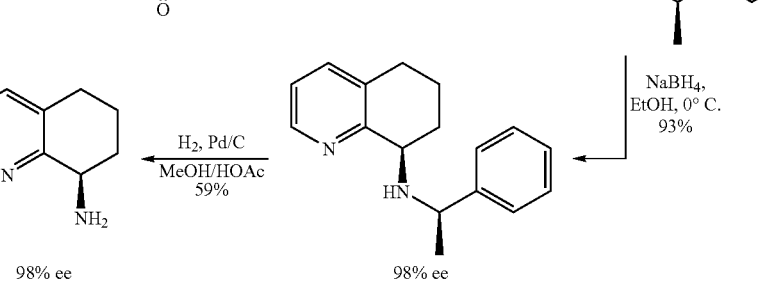

Note: Depending on which chiral auxiliary is employed (i.e. either (R)-(+)- or (S)-(−)-α-methylbenzylamine, both of which are commercially available), this method can be used to generate either (R)-(−)-8-amino-5,6,7,8-tetrahydroquinoline or (S)-(+)-8-amino-5,6,7,8-tetrahydroquinoline in enantiomerically pure form. The intermediate 8-hydroxy-5,6,7,8-tetrahydroquinoline was prepared according to the procedure described in Bridger et. al. PCT International application PCT/CA00/00321. For the purposes of illustration, the synthesis of (R)-(−)-8-amino-5,6,7,8-tetrahydroquinoline is described.

Preparation of 6,7-Dihydro-5H-quinolin-8-one

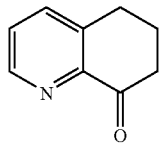

To a stirred solution of 8-hydroxy-5,6,7,8-tetrahydroquinoline (13.96 g, 93.6 mmol) in dry $CH_2Cl_2$ (400 mL) was added solid <5 micron activated 85% $MnO_2$ (manganese IV oxide) (82.22 g, 804 mmol). The resulting black suspension was stirred 18 h, at which point the mixture was filtered through a cake of celite and washed with $CH_2Cl_2$ (3×50 mL). The combined washings were concentrated to provide 11.27 g (82%) of the title compound as a pale yellow solid, which was used in subsequent reactions without further purification. This material displayed spectra identical to those reported above.

Preparation of (R)-(−)-(6,7-Dihydro-5H-quinolin-8-ylidene)-(1-phenylethyl)-amine

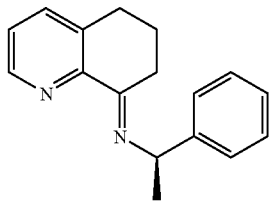

To a stirred solution of 6,7-dihydro-5H-quinolin-8-one (3.02 g, 20.5 mmol) in dry MeOH (100 mL) was added (R)-(+)-α-methylbenzylamine (2.61 mL, 20.5 mmol) via syringe. The resulting mixture was stirred 24 h, at which point additional (R)-(+)-α-methylbenzylamine (0.26 mL, 2.0 mmol) was added and the reaction was stirred for an additional 24 h. The solvent was removed in vacuo and dried for 3 days at room temperature under reduced pressure (0.1 Torr) to afford 5.38 g (95%) of the title compound as a red/brown solid. $[\alpha]_D$=−126.0 (c 1.04, $CHCl_3$); $^1H$ NMR ($CDCl_3$) δ 1.55 (d, 3H, J=6.9 Hz), 2.17–2.29 (m, 2H), 7.35 (t, 2H, J=7.8 Hz), 4.39 (q, 1H, J=6.6 Hz), 4.72 (t, 1H, J=4.7 Hz), 5.50 (br s, 1H), 7.07 (dd, 1H, J=7.5, 5.1 Hz) 7.20–7.47 (m, 6H), 8.37 (d, 1H, J=2.4 Hz); $^3C$ NMR ($CDCl_3$) δ 21.99, 25.68, 28.29, 53.79, 98.12, 122.43, 126.33, 127.03, 128.92, 132.63, 135.09, 139.47, 146.36, 150.48. ES-MS m/z 251 (M+H).

Preparation of (−)-(1-(R)-1-Phenylethyl)-(8-(R)-5,6,7,8-tetrahydroquinolin-8-yl)-amine

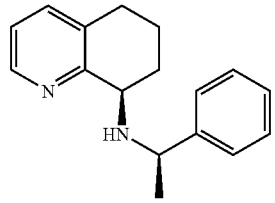

To a cold (0° C.), stirred solution of (R)-(−)-(6,7-dihydro-5H-quinolin-8-ylidene)-(1-phenylethyl)-amine (500 mg, 2.00 mmol) in dry ethanol (EtOH) (40 mL) was added solid $NaBH_4$ (sodium borohydride) (227 mg, 6.00 mmol) in one portion. The resulting mixture was stirred 3 h at 0° C., then slowly warmed to room temperature and stirred a further 18 h. Saturated aqueous $NaHCO_3$ (40 mL) was added and the phases were separated. The aqueous layer was extracted with $CH_2Cl_2$ (3×50 mL) and the combined organic extracts were dried ($MgSO_4$) and concentrated. Flash chromatography (silica gel, 20:2:1 $CHCl_3$—MeOH—$NH_4OH$) of the crude material afforded 470 mg (93%) of the title compound in 98% de (separated by chiral GC, J&W CycloSil B column, isothermal 180° C., (R,R)-diastereomer$_{rt}$=46.10 min, (S,R)-diastereomer$_{rt}$=46.92 min). $[\alpha]_D$=−31.0 (c 0.65, $CHCl_3$); $^1H$ NMR ($CDCl_3$) δ 1.48 (d, 3H, J=7 Hz), 1.55–1.64 (m, 2H), 2.65–2.79 (m, 3H), 3.86 (t, 1H, J=6 Hz), 4.10 (q, 1H, J=7 Hz), 7.05 (dd, 1H, J=8, 4 Hz), 7.14–7.46 (m, 6H), 8.42 (d, 1H, J=4 Hz); $^{13}C$ NMR ($CDCl_3$) δ 19.9, 24.7, 30.1, 31.1. 58.3, 58.8, 77.1, 77.5, 77.9, 122.4, 127.3, 127.5, 128.7, 137.4, 147.2. ES-MS m/z 253 (M+H).

Preparation of (R)-(−)-8-Amino-5,6,7,8-tetrahydroquinoline

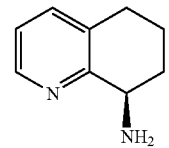

A solution of (−)-(1-(R)-1-phenylethyl)-(8-(R)-5,6,7,8-tetrahydroquinolin-8-yl)-amine (140 mg, 0.55 mmol) and acetic acid (127 μL, 2.20 mmol) in dry MeOH (3 mL) was flushed with nitrogen, then 10% palladium on carbon (32 mg) was added; the mixture was hydrogenated (50 psi) on a Parr Shaker for 18 h. The crude material was filtered through a cake of celite and washed with MeOH (3×10 mL) then the combined washings were concentrated. Flash chromatography (silica gel, 20:2:1 $CH_2Cl_2$-MeOH—$NH_4OH$) of the crude material afforded 49 mg (59%) of the title compound in 98% ee (separated by chiral GC, J&W CycloSil B column, initial temperature: 160° C., initial time: 0 min, rate: 1° C./min, final temperature: 130° C., final time: 0 min, (S)-(+)-enantiomer$_{rt}$=12.43 min, (R)-(−)-enantiomer$_{rt}$=13.13 min). $[\alpha]_D$=−124.3 (c 0.42, $CHCl_3$). The spectra of this material were identical to those reported above.

An additional example using (R)-(+)-1-phenylpropylamine as a chiral auxiliary is shown below.

Asymmetric Synthesis of (S)-(−)-8-Amino-5,6,7,8-tetrahydroquinoline using (S)-(−)-1-(4-Methoxyphenyl)ethylamine as Chiral Auxiliary

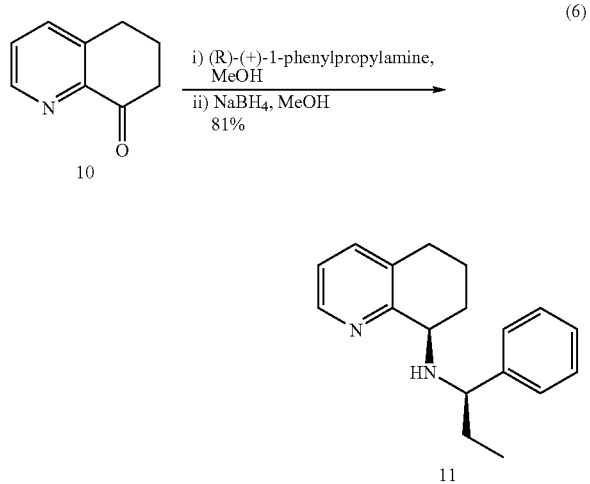

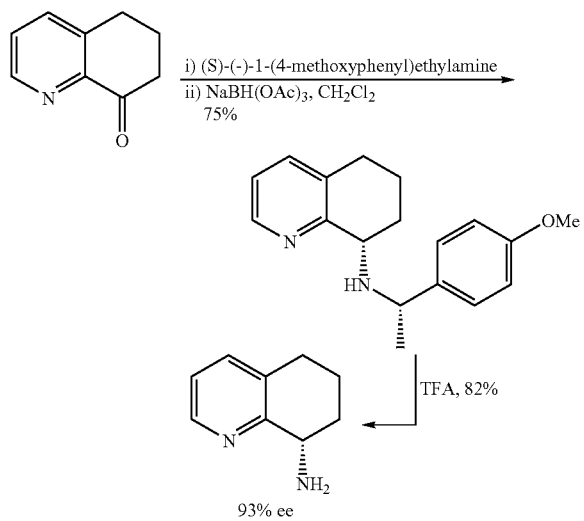

Preparation of (1-(S)-1-(4-Methoxyphenyl)ethyl)-(8-(S)-5,6,7,8-tetrahydroquinolin-8-yl)-amine

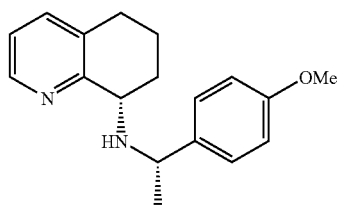

To a stirred solution of 6,7-dihydro-5H-quinolin-8-one (630 mg, 4.28 mmol) and (S)-(−)-1-(4-methoxyphenyl)ethylamine (647 mg, 4.28 mmol) in dry $CH_2Cl_2$ (15 mL) was added solid sodium triacetoxyborohydride (1.44 g, 6.42 mmol) in one portion. The resulting mixture was stirred for 16 h. At this time, 1N aqueous NaOH (10 mL) was added to quench the reaction. The layers were separated and the aqueous phase was extracted with $CH_2Cl_2$ (2×10 mL). The combined organic fractions were dried ($MgSO_4$) and then concentrated in vacuo. Flash chromatography (silica gel, ethyl acetate) of the residue thus obtained provided 905 mg (75%) of the title compound as a yellowish oil. $^1H$ NMR (300 MHz, $CDCl_3$) δ 8.49 (m, 1H), 7.37–7.30 (m, 3H), 7.04 (m, 1H), 6.84 (dd, J=3.3, 1.0 Hz, 1H), 4.03 (dd, J=6.6, 6.6 Hz), 3.85–3.78 (m, 4 H), 2.73–2.65 (m, 3H), 1.82–1.71 (m, 2H), 1.57–1.43 (m, 4H).

Preparation of (S)-(+)-8-Amino-5,6,7,8-tetrahydroquinoline

A round-bottom flask was charged with (1-(S)-1-(4-methoxyphenyl)ethyl)-(8-(S)-5,6,7,8-tetrahydroquinolin-8-yl)-amine (341 mg, 1.2 mmol) and trifluoroacetic acid (5 mL). The resulting solution was stirred at 60° C. for 4 h. At this time, most of the trifluoroacetic acid was removed in vacuo and the residue was taken up in $CH_2Cl_2$ (20 mL) and 5 N aqueous NaOH (10 mL) was added. The layers were separated and the aqueous phase was extracted with $CH_2Cl_2$ (3×20 mL). The combined organic layers were dried ($MgSO_4$) and concentrated in vacuo to give 146 mg (82%) of the title compound as a yellow oil in 93% ee (separated by chiral GC, J&W CycloSil B column, initial temperature: 160° C., initial time: 0 min, rate: 1° C./min, final temperature: 130° C., final time: 0 min, (S)-(+)-enantiomer$_{rt}$=12.43 min, (R)-(−)-enantiomer$_{rt}$=13.13 min. The spectra of this material were identical to those reported above.

Other compounds were prepared based upon the above processes and are:

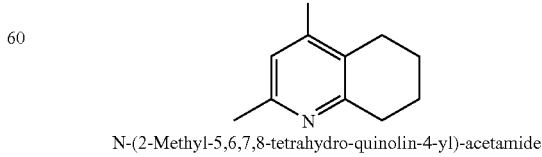

N-(2-Methyl-5,6,7,8-tetrahydro-quinolin-4-yl)-acetamide

-continued

N-(1,2,3,4-Tetrahydro-quinolin-7-yl)-acetamide

N-(5,6,7,8-tetrahydroquinolin-8-yl)-acetamide (R,S)-N-(2-Methyl-5,6,7,8-tetrahydro-quinolin-8-yl)-acetamide 1,2,3,4-Tetrahydro-quinoline-8-carboxylic acid methyl ester (R,S)-N-(2-Methyl-1,2,3,4-tetrahydro-quinolin-8-yl)-acetamide 3-Methoxy-5,6,7,8-tetrahydro-quinoline (R,S)-8-Amino-2-methyl-5,6,7,8-tetrahydroquinoline (R)-N-(2-Methyl-5,6,7,8-tetrahydro-quinolin-8-yl)-acetamide -continued (S)-8-Amino-2-methyl-5,6,7,8-tetrahydroquinoline (S)-5-Amino-5,6,7,8-tetrahydroquinoline (R)-N-(5,6,7,8-tetrahydro-quinolin-5-yl)-acetamide (S)-6-Amino-5,6,7,8-tetrahydroquinoline (R)-N-(5,6,7,8-tetrahydro-quinolin-6-yl)-acetamide (R,S)-5-Amino-5,6,7,8-tetrahydroisoquinoline (S)-5-Amino-5,6,7,8-tetrahydroisoquinoline (R)-N-(5,6,7,8-tetrahydro-isoquinolin-5-yl)-acetamide (S)-6,7-Dihydro-5H-[1]pyrindin-7-ylamine

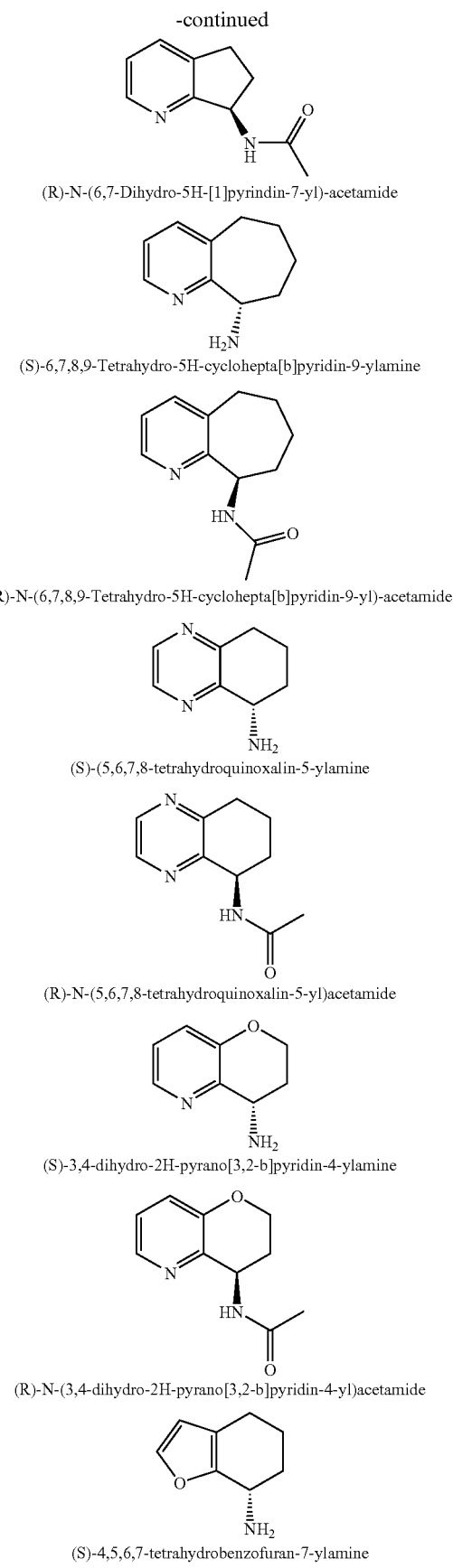

(R)-N-(6,7-Dihydro-5H-[1]pyrindin-7-yl)-acetamide (S)-6,7,8,9-Tetrahydro-5H-cyclohepta[b]pyridin-9-ylamine (R)-N-(6,7,8,9-Tetrahydro-5H-cyclohepta[b]pyridin-9-yl)-acetamide (S)-(5,6,7,8-tetrahydroquinoxalin-5-ylamine (R)-N-(5,6,7,8-tetrahydroquinoxalin-5-yl)acetamide (S)-3,4-dihydro-2H-pyrano[3,2-b]pyridin-4-ylamine (R)-N-(3,4-dihydro-2H-pyrano[3,2-b]pyridin-4-yl)acetamide (S)-4,5,6,7-tetrahydrobenzofuran-7-ylamine

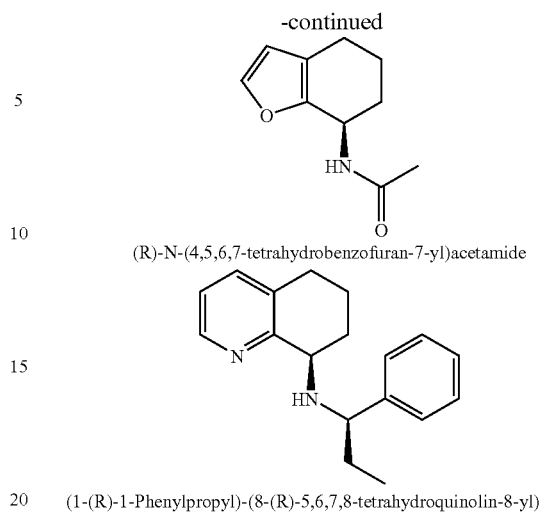

(R)-N-(4,5,6,7-tetrahydrobenzofuran-7-yl)acetamide (1-(R)-1-Phenylpropyl)-(8-(R)-5,6,7,8-tetrahydroquinolin-8-yl)-amine It is understood that the examples and embodiments described herein are for illustrative purposes only and that various modifications or changes in light thereof will be suggested to persons of skill in the art and are to be incorporated within the spirit and purview of this application and the scope of the claims. All publications, patents, and patent applications cited herein are hereby incorporated by reference.

Citation of the above documents is not intended as an admission that any of the foregoing is pertinent prior art, nor does it constitute any admission as to the contents or date of these documents.

We claim:

1. A process for synthesizing an enantiomer of a primary amino-substituted fused bicyclic ring of formula IX comprising:

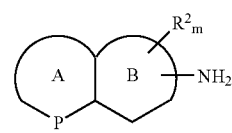

IX a) forming the Schiff base of a keto group located on ring B of the fused bicyclic ring by reacting it with an enantiomerically-pure primary amine chiral auxiliary R*NH$_2$ of the formula X

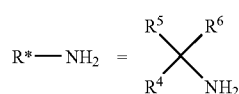

X to produce the corresponding enantiomerically-pure imine of the fused bicyclic ring;

b) diastereoselectively reducing the imine to produce the corresponding enantiomerically-pure secondary amine on the fused bicyclic ring; and c) removing the chiral auxiliary R* to form the enantiomer of the primary amino-substituted fused bicyclic ring;

wherein ring A is a heteroaromatic 5- or 6-membered ring, P is a nitrogen atom, sulfur atom or oxygen atom; ring B is a 5- or 6-membered cycloalkyl or heterocycloalkyl;

wherein $NH_2$ is located at a position on ring B; and $R_2$ is located at any other hydrogen position on the fused bicyclic ring;

wherein m is 0–4; $R^2$ is selected from the group consisting of halo, nitro, cyano, carboxylic acid, alkyl, alkenyl, cycloalkyl, hydroxyl, thiol, a protected amino, acyl, carboxylate, carboxamide, sulfonamide, an aromatic group and a heterocyclic group; and $R^4$, $R^5$, and $R^6$ are each different and selected from the group consisting of hydrogen, alkyl, alkenyl, cycloalkyl, cycloalkenyl, and a 5- or 6-membered aromatic ring; and at least one of $R^4$, $R^5$, or $R^6$ is a 5- or 6-membered aromatic or heteroaromatic ring.

2. The process of claim 1 wherein the keto group is formed by oxidizing a corresponding hydroxyl group located on ring B of the fused bicyclic ring.

3. The process of claim 1 wherein the enantiomerically-pure primary amine chiral auxiliary is selected from the group consisting of phenylethylamine, naphthylethylamine, phenylpropylamine, and methoxyphenylethylamine.

4. The process of claim 3 wherein the enantiomerically-pure primary amine chiral auxiliary is (R)-(+)-phenylethylamine, (R)-(+) 1 -phenylpropylamine, or (S)-(−)-1-(4-methoxyphenyl)ethylamine.

5. The process of claim 1 wherein the imine is reduced by a boron-based hydride reducing agent, an aluminum-based hydride agent, or hydrogen with a metal catalyst.

6. The process of claim 1 wherein the chiral auxiliary R* is removed by hydrogenation or acid-mediated cleavage.

7. The process of claim 1 wherein the fused bicyclic ring is a quinoline or an isoquinoline.

8. The process of claim 1, wherein the $NH_2$ is located at the 8-position on the quinoline and at the 5-position on the isoquinoline.

9. The process of claim 8, wherein m is 0 or 1.

10. The process of claim 9, wherein $R^2$ is methyl.

* * * * *